(12) United States Patent
Shetty et al.

(10) Patent No.: US 11,707,577 B2
(45) Date of Patent: Jul. 25, 2023

(54) ACCURATE, PRECISE MICROLITER DOSING SYRINGE

(71) Applicants: Santen Pharmaceutical Co., Ltd., Osaka (JP); Congruence Medical Solutions, LLC, Hanover, MD (US)

(72) Inventors: Gautam N. Shetty, Hanover, MD (US); Lou Castagna, Middletown, PA (US)

(73) Assignees: Santen Pharmaceutical Co., Ltd., Osaka (JP); Congruence Medical Solutions, LLC, Hanover, MD (US)

( * ) Notice: Subject to any disclaimer, the term of this patent is extended or adjusted under 35 U.S.C. 154(b) by 1319 days.

(21) Appl. No.: 16/093,121

(22) PCT Filed: Apr. 7, 2017

(86) PCT No.: PCT/US2017/026684
§ 371 (c)(1),
(2) Date: Oct. 11, 2018

(87) PCT Pub. No.: WO2017/180480
PCT Pub. Date: Oct. 19, 2017

(65) Prior Publication Data
US 2021/0178080 A1   Jun. 17, 2021

Related U.S. Application Data

(60) Provisional application No. 62/323,341, filed on Apr. 15, 2016.

(51) Int. Cl.
*A61M 5/00* (2006.01)
*A61M 35/00* (2006.01)
(Continued)

(52) U.S. Cl.
CPC ....... *A61M 5/31551* (2013.01); *A61F 9/0008* (2013.01); *A61M 5/3129* (2013.01);
(Continued)

(58) Field of Classification Search
CPC ............. A61F 9/0008; A61M 5/31575; A61M 5/31558; A61M 5/31511; A61M 5/31533; A61M 5/315; A61M 5/31551
See application file for complete search history.

(56) References Cited

U.S. PATENT DOCUMENTS

| 3,122,280 A | 2/1964 | Goda |
| 3,770,026 A | 11/1973 | Isenberg |

(Continued)

FOREIGN PATENT DOCUMENTS

| CN | 101932350 | 12/2010 |
| EA | 201590139 A1 | 7/2015 |

(Continued)

OTHER PUBLICATIONS

Notification of Reasons for Refusal dated Sep. 14, 2021, directed to JP Application No. 2019-505122; 16 pages.

(Continued)

*Primary Examiner* — Rebecca E Eisenberg
(74) *Attorney, Agent, or Firm* — Morrison & Foerster LLP

(57) ABSTRACT

According to some embodiments, a syringe may include a barrel; a delivery conduit; a plunger seal disposed within the barrel; and a plunger rod assembly affixed to an end of the barrel, the plunger rod assembly including a first plunger rod component comprising a first linear gear, a second plunger rod component disposed at least partially in the barrel and engaged with the plunger seal, wherein the second plunger rod component comprises a second linear gear, a first rotational gear having a plurality of gear teeth for engaging the first linear gear, and a second rotational gear having a second plurality of gear teeth for engaging the second linear gear, wherein the first rotational gear is coupled to the second rotational gear such that translation of the first (Continued)

plunger rod component causes translation of the second plunger rod component.

27 Claims, 23 Drawing Sheets

(51) Int. Cl.
*A61M 5/315* (2006.01)
*A61F 9/00* (2006.01)
*A61M 5/31* (2006.01)
*A61M 5/34* (2006.01)
*A61M 37/00* (2006.01)
*A61M 39/10* (2006.01)

(52) U.S. Cl.
CPC .... *A61M 5/31558* (2013.01); *A61M 5/31575* (2013.01); *A61M 5/31585* (2013.01); *A61M 5/34* (2013.01); *A61M 37/0015* (2013.01); *A61M 39/10* (2013.01); *A61M 2005/3131* (2013.01)

(56) References Cited

U.S. PATENT DOCUMENTS

| | | | |
|---|---|---|---|
| 4,073,321 | A | 2/1978 | Moskowitz |
| 4,244,366 | A | 1/1981 | Raines |
| 4,563,178 | A | 1/1986 | Santeramo |
| 4,921,487 | A | 5/1990 | Buffet et al. |
| 4,929,238 | A | 5/1990 | Baum |
| 5,104,380 | A | 4/1992 | Holman et al. |
| 5,318,544 | A | 6/1994 | Drypen et al. |
| 5,782,633 | A * | 7/1998 | Muhlbauer ....... B05C 17/00509 222/326 |
| 5,951,526 | A | 9/1999 | Korisch et al. |
| 7,678,084 | B2 | 3/2010 | Judson et al. |
| 8,535,277 | B2 | 9/2013 | Oden et al. |
| 8,915,889 | B2 | 12/2014 | Cox et al. |
| 9,956,351 | B2 | 5/2018 | Møller |
| 2004/0162528 | A1 | 8/2004 | Horvath et al. |
| 2005/0165363 | A1* | 7/2005 | Judson ............ A61M 5/31551 604/209 |
| 2005/0215957 | A1 | 9/2005 | Hynes |
| 2006/0217670 | A1* | 9/2006 | Cecchi ................ A61M 5/19 604/209 |
| 2007/0073224 | A1 | 3/2007 | Dries |
| 2012/0041366 | A1 | 2/2012 | Fayyaz et al. |
| 2012/0053516 | A1 | 3/2012 | Cronenberg et al. |
| 2012/0172815 | A1 | 7/2012 | Holmqvist |
| 2012/0172816 | A1 | 7/2012 | Boyd et al. |
| 2013/0150803 | A1 | 6/2013 | Shetty et al. |
| 2013/0204193 | A1 | 8/2013 | Holmqvist |
| 2013/0267908 | A1 | 10/2013 | Leak et al. |
| 2014/0012227 | A1 | 1/2014 | Sigg |
| 2018/0056009 | A1 | 3/2018 | Filman et al. |
| 2018/0126085 | A1 | 5/2018 | Bowman et al. |
| 2018/0200446 | A1 | 7/2018 | Grimoldby et al. |
| 2021/0146058 | A1 | 5/2021 | Shetty |

FOREIGN PATENT DOCUMENTS

| | | | |
|---|---|---|---|
| EP | 0058536 | A1 | 8/1982 |
| EP | 0584531 | A2 | 3/1994 |
| EP | 0800798 | A1 | 10/1997 |
| JP | 2005520646 | A | 7/2005 |
| JP | 2015-131114 | A | 7/2015 |
| KR | 10-2009-0080560 | A | 7/2009 |
| KR | 10-2009-0082489 | A | 7/2009 |
| KR | 10-2014-0105457 | A | 9/2014 |
| RU | 2011127107 | A | 1/2013 |
| TW | 201315502 | | 4/2013 |
| WO | 03/080160 | A1 | 10/2003 |
| WO | WO2008101829 | A1 | 8/2008 |
| WO | 2009154803 | A2 | 12/2009 |
| WO | 2009154803 | A3 | 3/2010 |
| WO | 2010063687 | A1 | 6/2010 |
| WO | 2011/088894 | A1 | 7/2011 |
| WO | 2014005728 | A1 | 1/2014 |
| WO | WO-2015007811 | A * | 1/2015 .............. A61M 5/20 |
| WO | 2015/052704 | A1 | 4/2015 |
| WO | 2018/141633 | A1 | 8/2018 |
| WO | 2018/141634 | A1 | 8/2018 |

OTHER PUBLICATIONS

Office Action dated Oct. 29, 2021, directed to KR Application No. 10-2018-7031807; 7 pages.
Extended European Search Report, dated Sep. 20, 2019, for European Patent Application No. 17782891.0, 9 pages.
Examination Report dated Jun. 30, 2021, directed to IN Application No. 201817038141; 5 pages.
International Search Report and Written Opinion dated Jun. 17, 2021, directed to International Application No. PCT/US2020/060589; 24 pages.
Office Action dated May 4, 2021, directed to TW Application No. 106112496; 14 pages.
International Preliminary Report on Patentability received for PCT Patent Application No. PCT/US2017/026684, dated Oct. 25, 2018, 8 pages.
International Search Report and Written Opinion received for PCT Patent Application No. PCT/US2017/026684, dated Jun. 19, 2019, 10 pages.
Extended European Search Report dated Mar. 9, 2021, directed to EP Application No. 21152295; 10 pages.
Invitation to Pay Additional Fees dated Mar. 9, 2021, directed to International Application No. PCT/US2020/060589; 14 pages.
Notification of Reasons for Refusal dated Feb. 2, 2021, directed to JP Application No. 2019-505122; 19 pages.
Notification of the First Office Action dated Sep. 25, 2020, directed to CN Application No. 201780023860.9; 24 pages.
Notification of the Second Office Action dated Mar. 17, 2021, directed to CN Application No. 201780023860.9; 6 pages.
Official Action dated Jul. 24, 2020, directed to RU Application No. 2018139650; 24 pages.
Shetty et al., U.S. Appl. No. 17/098,276, filed Nov. 13, 2020 for "Variable Dosing Syringe." [A copy is not submitted herewith pursuant to the waiver of 37 C.F.R. § 1.98(a)(2)(iii) issued by the Office on Sep. 21, 2004.].
Decision to Grant a Patent dated Mar. 29, 2022, directed to JP Application No. 2019-505122; 5 pages.
Decision to Grant dated Jan. 11, 2021, directed to EP Application No. 17782891,0; 3 pages.
Decision to Grant dated Oct. 28, 2020, directed to RU Application No. 2018139650; 30 pages.
Intention to Grant dated Aug. 28, 2020, directed to EP Application No. 17782891.0; 7 pages.
Notice of Allowance dated Jan. 24, 2022, directed to KR Application No. 10-2018-7031807; 7 pages.
Notice of Allowance dated Jun. 25, 2021, directed to CN Application No. 201780023860.9; 6 pages.
Office Action dated Sep. 30, 2019, directed to TH Application No. 1801006231; 4 pages.

* cited by examiner

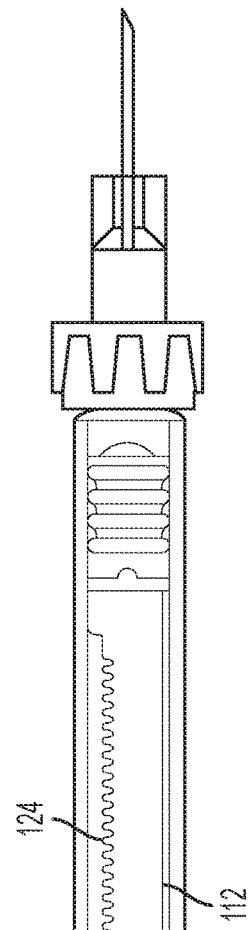
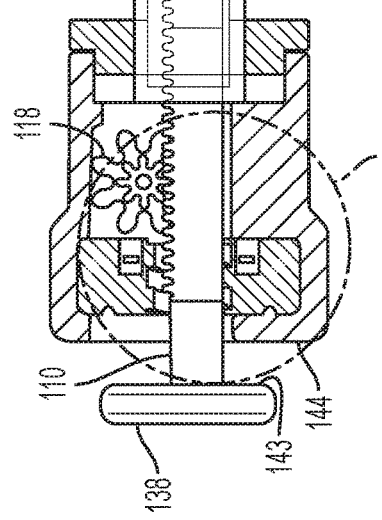
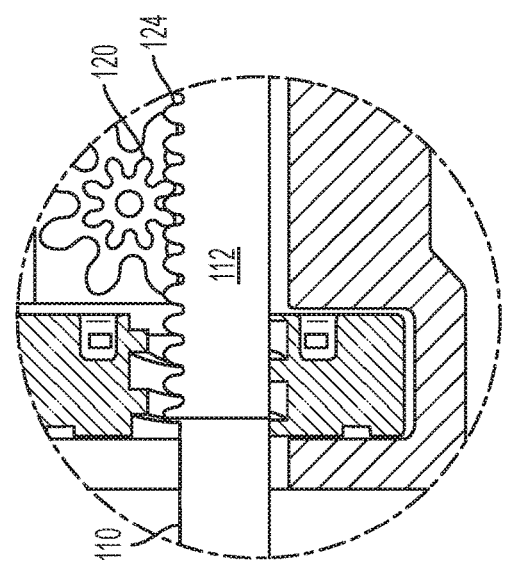
FIG. 10A
FIG. 10B

ACCURATE, PRECISE MICROLITER DOSING SYRINGE

CROSS REFERENCE TO RELATED APPLICATIONS

This application is a national stage application under 35 U.S.C. § 371 of International Application No. PCT/US2017/026684, filed internationally on Apr. 7, 2017, which claims priority to U.S. Provisional Application Ser. No. 62/323,341, filed Apr. 15, 2016, titled "Accurate, Precise Microliter Dosing Syringe," each of which is hereby incorporated by reference in its entirety.

FIELD OF THE INVENTION

This invention relates to syringes and, more specifically, to syringes that can deliver microliter-sized doses.

BACKGROUND OF THE INVENTION

Studies have shown that a number of factors contribute towards inability of standard syringes to deliver accurate and precise microliter sized doses. Most conventional syringes, which include components such as a cylindrical barrel, a plunger rod, and a plunger seal, are designed to deliver milliliter doses and are unable to deliver an accurate and precise dose. Variation in delivering microliter-sized doses using a conventional syringe are often caused by the inability of the user to precisely control the distance of travel by the plunger rod. Travel distance is controlled by setting the start of the dose and the end of the dose. Studies have shown that providing a better defined start and end of the dose can improve accuracy of delivering a microliter dose. However, this is insufficient to ensure precision. Imprecision can be due to variability from one user to another and to inherent human limitations in establishing limits and resolution of the travel distance. Studies have shown that this variation could be as much as 20% of the intended dose. Further, manufacturing issues may cause variations when establishing visual references and markings that define plunger travel. These variations are negligible when delivering milliliter sized doses, but are significant source of variation when delivering microliter sized doses.

Many clinical and non-clinical applications require that a microliter sized dose be delivered. Applications for microliter delivery include injectable drug delivery into or onto the eye, intracellular delivery, delivery of radioactive agents, chemotherapy, etc. Both accuracy and precision are important with drugs that have a small therapeutic window, and where inadequate accuracy and precision would put the amount of injected drug outside of its therapeutic window. In some cases, inaccuracy and imprecision can cause alterations in biophysical properties at the injected site, such as increase in pressure, rupture of cell walls, etc. In the case of microliter delivery of drugs, systems that are not compatible with either standard pharmaceutical fill-finish systems or standard prefillable syringe components may be unsuitable. Studies have shown that used of microliter delivery systems for intravitreous administration with only conventional prefillable syringe components results in a suboptimal outcome.

Irrespective of whether an injectable substance or drug is prefilled or user-filled, a microliter dosing syringe should be able to prime the needle or any other delivery conduit to ensure that any air is expelled before delivery. Priming is important to ensure that once the dose is set, an accurate dose is dispensed. In instances where the drug is prefilled (i.e. not filled by the end user), the ability to prime is critical to ensuring that the accuracy of the administered dose is independent of the accuracy of the drug fill.

There is a need for accurate, precise microliter dose setting and delivery mechanisms adaptable to conventional, commercially available syringes—thereby enabling a conventional syringe to deliver accurate, precise microliter volumes.

SUMMARY OF THE INVENTION

According to some embodiments, accurate and precise dosing mechanisms can be configured with a number of syringe configurations, including: prefilled (with pre-attached needle, with user-attached needle, with a retractable needle, etc.) and user filled. According to some embodiments, a system includes a dosing mechanism that is manufactured and partly assembled independent of the syringe and then coupled to the syringe to provide the plunger rod functionality. As such, the functioning of the accurate dosing mechanism may include features analogous to those of a plunger rod in a conventional syringe but with improved resolution of dose setting for accurate and precise microliter dose delivery.

According to some embodiments, the system may include a plunger rod with lugs and teeth. The lugs on the plunger rod may mechanically interact with internal threads within the thumb nut. The teeth of the plunger rod may mesh with a set of teeth of a gear of a gear train. Axial advancement of the plunger rod may generate a torsional force that causes rotation of the gear. The gear may be coupled with one or more additional gears. The teeth of one of the additional gears may mesh with the teeth of a drive rod. The drive rod may be placed within a prefilled syringe barrel and may abut a plunger adapter. The plunger adapter may be screwed into the back of a plunger seal. The thumb nut and gear train are all placed within a housing. The gear may be attached to the housing by way of a pin at its geometric center. The flange of the syringe barrel may be placed within the housing and a cover may mate with the housing to couple the dosing mechanism to the syringe.

According to some embodiments, a plunger rod assembly for a syringe includes a first plunger rod component comprising a first linear gear, a second plunger rod component comprising a second linear gear, a first rotational gear having a plurality of gear teeth for engaging the first linear gear, and a second rotational gear having a second plurality of gear teeth for engaging the second linear gear, wherein the first rotational gear is coupled to the second rotational gear such that translation of the first plunger rod component causes translation of the second plunger rod component.

In any of these embodiments, translation of the first plunger rod component a first amount may cause translation of the second plunger rod component a second amount that is less than the first amount. In any of these embodiments, the first rotational gear and the second rotational gear may be portions of a compound gear.

In any of these embodiments, the first rotational gear may be spaced from the second rotational gear. In any of these embodiments, the first and second rotational gears may be spaced by a third rotational gear. In any of these embodiments, the second and third rotational gears may be compound gears.

In any of these embodiments, the first set of gear teeth may have a first pitch diameter and the second set of gear teeth may have a second pitch diameter that is different from the first pitch diameter. In any of these embodiments, the first pitch diameter may be greater than the second pitch diameter.

In any of these embodiments, at least one of the first and second sets of gear teeth may include involute gear teeth. In any of these embodiments, the first and second plunger rod components may be configured for at least partial insertion into a barrel of a syringe. In any of these embodiments, at least a portion of the first plunger rod component may include a semicircular cross section and at least a portion of the second plunger rod component may include a complimentary semicircular cross section. In any of these embodiments, the first plunger rod component may include at least one protrusion and the assembly may further include a rotational component for engaging the at least one protrusion.

In any of these embodiments, the first plunger rod component may be configured to axially translate in response to rotation of the rotational component when the rotational component is engaged with at least one of the at least one protrusion. In any of these embodiments, the first plunger rod component may be configured to axially translate in response to a force having an axial component applied directly to the first plunger rod component after the rotational component disengages from the at least one protrusion.

In any of these embodiments, the rotational component may include an internal thread for engaging the at least one protrusion. In any of these embodiments, the rotational component may include at least one stop that engages one of the at least one protrusion when the plunger rod component reaches an axial position relative to the rotational component. In any of these embodiments, the assembly may include at least one ratchet component that is engaged with the rotational component such that the rotational component is prevented from rotating in one direction. In any of these embodiments, the assembly may include at least one ratchet component that is engaged with the rotational component such that the rotational component rotates more freely in a first direction than in a second direction.

In any of these embodiments, the assembly may include a housing for mounting on an end of a syringe barrel. In any of these embodiments, the assembly may include a retainer for engaging with the housing and the end of the syringe barrel for affixing the plunger rod assembly to the end of the syringe barrel. In any of these embodiments, the retainer may affix to the housing. In any of these embodiments, the retainer may engage with an internal thread or groove in the recess of the housing. In any of these embodiments, the first plunger rod component may extend through an aperture in the housing, and the perimeter of the aperture may engage with the first plunger rod component to prevent rotation of the first plunger rod component.

According to some embodiments, a syringe may include a barrel; a delivery conduit; an elastomeric or elastomer containing plunger seal disposed within the barrel; and a plunger rod assembly affixed to an end of the barrel, the plunger rod assembly including a first plunger rod component comprising a first linear gear, a second plunger rod component disposed at least partially in the barrel and engaged with the plunger seal, wherein the second plunger rod component comprises a second linear gear, a first rotational gear having a plurality of gear teeth for engaging the first linear gear, and a second rotational gear having a second plurality of gear teeth for engaging the second linear gear, wherein the first rotational gear is coupled to the second rotational gear such that translation of the first plunger rod component causes translation of the second plunger rod component.

In any of these embodiments, axial translation of the first plunger rod component a first amount may cause axial translation of the second plunger rod component a second amount that is less than the first amount. In any of these embodiments, the first rotational gear and the second rotational gear may be portions of a compound gear. In any of these embodiments, the first rotational gear may be spaced from the second rotational gear.

In any of these embodiments, the first and second rotational gears may be spaced by a third rotational gear. In any of these embodiments, the second and third rotational gears may be compound gears. In any of these embodiments, the first set of gear teeth may have a first pitch diameter and the second set of gear teeth may have a second pitch diameter that is different from the first pitch diameter. In any of these embodiments, the first pitch diameter may be greater than the second pitch diameter. In any of these embodiments, at least one of the first and second sets of gear teeth may include involute gear teeth. In any of these embodiments, the first and second plunger rod components may be configured for at least partial insertion into a barrel of a syringe.

In any of these embodiments, at least a portion of the first plunger rod component may include a semicircular cross section and at least a portion of the second plunger rod component may include a complimentary semicircular cross section. In any of these embodiments, the first plunger rod component may include at least one protrusion and the assembly may further include a rotational component for engaging the at least one protrusion.

In any of these embodiments, the first plunger rod component may be configured to axially translate in response to rotation of the rotational component when the second rotational component is engaged with at least one of the at least one protrusion. In any of these embodiments, the first plunger rod component may be configured to axially translate in response to a force having an axial component applied directly to the first plunger rod component after the rotational component disengages from the at least one protrusion.

In any of these embodiments, the rotational component may include an internal thread for engaging the at least one protrusion. In any of these embodiments, the rotational component may include at least one stop that engages one of the at least one protrusion when the plunger rod component reaches an axial position relative to the rotational component. In any of these embodiments, the assembly may include at least one ratchet component that is engaged with the rotational component such that the rotational component is prevented from rotating in one direction. In any of these embodiments, the assembly may include at least one ratchet component that is engaged with the rotational component such that the rotational component rotates more freely in a first direction than in a second direction. In any of these embodiments, the assembly may include a housing mounted on an end of the barrel.

In any of these embodiments, the assembly may include a retainer that is engaged with the housing and the end of the barrel to affix the plunger rod assembly to the end of the syringe barrel. In any of these embodiments, the retainer may affix to the housing. In any of these embodiments, the retainer may engage with an internal thread or groove in the recess of the housing. In any of these embodiments, the first plunger rod component may extend through an aperture in the housing, and the perimeter of the aperture may engage with the first plunger rod component to prevent rotation of the first plunger rod component. In any of these embodiments, the syringe may be a prefilled or a prefillable syringe.

In any of these embodiments, the delivery conduit may include an attached needle, an attachable needle, an IV connector, an attachable tubing connector, or an attachable microneedle array. In any of these embodiments, the plunger seal may include an adapter for engagement with the second plunger rod component.

According to some embodiments, a plunger rod assembly for a syringe includes a first plunger rod component; and a second plunger rod component configured to translate relative to the first plunger rod component, wherein the second plunger rod component engages with the first plunger rod component such that the second plunger rod component translates in response to translation of the first plunger rod component.

In any of these embodiments, the second plunger rod component may engage with the first plunger rod component through at least one rotational gear. In any of these embodiments, the first plunger rod component may include a first linear gear; the second plunger rod component may include a second linear gear; and the at least one rotational gear may include a first gear having a first set of gear teeth for engaging the first linear gear and a second gear having a second set of gear teeth for engaging the second linear gear.

In any of these embodiments, the first gear and the second gear may be portions of a compound gear. In any of these embodiments, the first gear may be spaced from the second gear. In any of these embodiments, the assembly may further include a rotational component configured to engage with the first plunger rod component such that rotation of the rotational component causes axial translation of the first plunger rod component.

In any of these embodiments, the rotational component may include an internal thread for engaging one or more protrusions on the first plunger rod component. In any of these embodiments, the second plunger rod component engages with the first plunger rod component such that the second plunger rod component axially translates a first amount in response to axial translation of the first plunger rod component a second amount that is greater than the first amount.

In any of these embodiments, the assembly may include at least one ratchet or ratchet-like component that is engaged with the rotational component such that the rotational component is prevented from rotating in one direction. In any of these embodiments, the assembly may include at least one ratchet component that is engaged with the rotational component such that the rotational component rotates more freely in a first direction than in a second direction. In any of these embodiments, the assembly may include a housing for mounting on a non-patient end of a syringe barrel. In any of these embodiments, the assembly may include a retainer for engaging with the housing and the non-patient end of the syringe barrel for affixing the plunger rod assembly to the non-patient end of the syringe barrel.

In any of these embodiments, the first plunger rod component may extend through an aperture in the housing, and the perimeter of the aperture may be shaped to prevent rotation of the first plunger rod component.

According to some embodiments, a syringe includes a barrel; a delivery conduit; a plunger seal disposed within the barrel; and a plunger rod assembly affixed to an end of the barrel, the plunger rod assembly including a first plunger rod component; and a second plunger rod component disposed at least partially in the barrel and engaged with the plunger seal, wherein the second plunger rod component is configured to axially translate relative to the first plunger rod component and engages with the first plunger rod component such that the second plunger rod component axially translates in response to translation of the first plunger rod component.

In any of these embodiments, the second plunger rod component may engage with the first plunger rod component through at least one rotational gear. In any of these embodiments, the first plunger rod component may include a first linear gear; the second plunger rod component may include a second linear gear; and the at least one rotational gear may include a first gear having a first set of gear teeth for engaging the first linear gear and a second gear having a second set of gear teeth for engaging the second linear gear.

In any of these embodiments, the first gear and the second gear may be portions of a compound gear. In any of these embodiments, the first gear may be spaced from the second gear. In any of these embodiments, the syringe may further include a rotational component configured to engage with the first plunger rod component such that rotation of the rotational component causes axial translation of the first plunger rod component. In any of these embodiments, the rotational component may include an internal thread for engaging one or more protrusions on the first plunger rod component.

In any of these embodiments, the second plunger rod component may engage with the first plunger rod component such that the second plunger rod component translates a first amount in response to translation of the first plunger rod component a second amount that is greater than the first amount. In any of these embodiments, the assembly may include at least one ratchet component that is engaged with the rotational component such that the rotational component is prevented from rotating in one direction. In any of these embodiments, the assembly may include at least one ratchet component that is engaged with the rotational component such that the rotational component rotates more freely in a first direction than in a second direction.

In any of these embodiments, the assembly may include a housing mounted on an end of the barrel. In any of these embodiments, the assembly may include a retainer that is engaged with the housing and the end of the barrel to affix the plunger rod assembly to the end of the syringe barrel. In any of these embodiments, the first plunger rod component may extend through an aperture in the housing, and the perimeter of the aperture may be shaped to prevent rotation of the first plunger rod component. In any of these embodiments, the syringe may be a prefilled syringe.

In any of these embodiments, the delivery conduit may include an attached needle, an attachable needle, an attachable tubing connector, or an attachable microneedle array. In any of these embodiments, the plunger seal may include an adapter for engagement with the second plunger rod component.

According to some embodiments, a blister pack includes a pre-filled syringe according to any of the above embodiments, wherein the syringe has been sterilized using EtO, H2O2, NO2 or Vaporized Peracetic Acid.

In any of these embodiments, the outer surface of the syringe may have at most 1 ppm EtO, H2O2, NO2 or Vaporized Peracetic Acid. In any of these embodiments, the total EtO, H2O2, NO2 or Vaporized Peracetic Acid residue on the outside of the syringe and inside of the blister pack may be at most 0.1 mg. In any of these embodiments, the syringe may have been sterilized with a Sterility Assurance Level of at least $10^{-6}$.

According to some embodiments, a method of delivering a dosage using a syringe according to any of the above embodiments includes while pointing the delivery conduit of the syringe upwards with respect to the barrel, advancing the plunger seal within the barrel by rotating the rotational component; setting a dosage by continuing to rotate the rotational component until the rotational component disengages from the first plunger rod; and after the rotational component disengages from the first plunger rod, delivering the dosage by applying a user force directly to an end of the first plunger rod to advance the plunger seal.

In any of these embodiments, the method may include attaching a needle to the syringe prior to advancing the plunger seal within the barrel by rotating the second rotational component. In any of these embodiments, the syringe may be a prefilled syringe.

In any of these embodiments, the prefilled syringe may be filled with a drug used for ophthalmic applications. In any of these embodiments, the number of 10 micrometer or larger sized sub-visible particulates may be less than 50 per milliliter of drug solution. In any of these embodiments, the number of 25 micrometer or larger sized sub-visible particulates may be less than 5 per milliliter of the drug solution. In any of these embodiments, the number of 50 micrometer or larger sized sub-visible particulates may be less than 2 per milliliter of the drug solution.

BRIEF DESCRIPTION OF THE DRAWINGS

The invention will now be described, by way of example only, with reference to the accompanying drawings, in which:

FIGS. 10A and 10B are cross-sectional views illustrating the dose set configuration of a system, according to an embodiment;

DETAILED DESCRIPTION OF EXEMPLARY EMBODIMENTS

Figure 1:
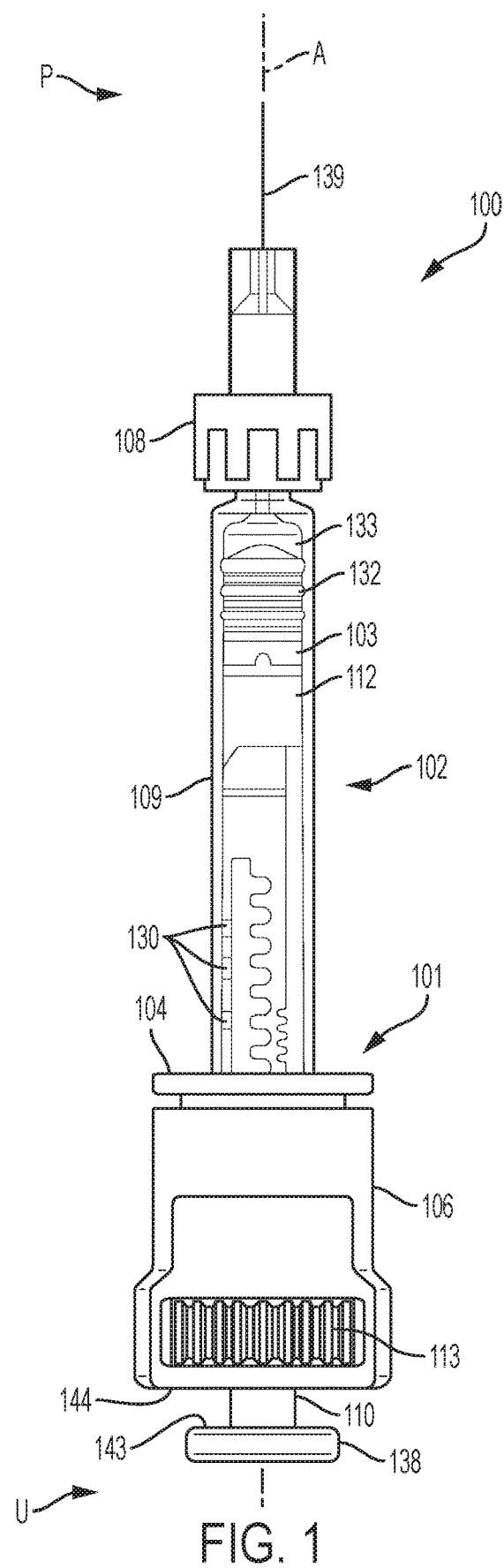
FIG. 1 is a side view of a dosing syringe system, according to a first embodiment.

Described herein are accurate and precise dosing mechanisms and systems incorporating the mechanisms with conventional (or custom) syringe bodies to provide an accurate and precise dosing syringe. According to some embodiments, the dosing mechanism translates user action into precisely controlled movements of a multi-component plunger rod. A gear train may couple plunger rod components such that the axial distance travelled by the plunger rod component that pushes on a syringe plunger seal is reduced relative to the axial distance travelled by the plunger rod component with which the user directly engages. A thumb nut engages with one of the plunger rod components to precisely control the travel distances of the plunger rod components. The dosing mechanism can include one or more features for coupling the mechanism to the plunger seal end of a conventional syringe.

The below description is provided to assist in an understanding of exemplary embodiments of the present disclosure with reference to the accompanying figures. Accordingly, those of ordinary skill in the art will recognize that various changes to and modifications of the exemplary embodiments described herein can be made without departing from the scope of the claimed invention. Also, descriptions of generally well-known functions and constructions are omitted for conciseness.

As used herein to describe the mechanism to deliver an accurate, precise dose, drug delivery syringes, or any of the relative positions of the components of the present invention, the terms "axial" or "axially" refer generally to a longitudinal axis "A" around which the mechanisms and syringes may be positioned, although not necessarily symmetrically. The term "radial" refers generally to all directions orthogonal to axis "A". The term user end refers generally to the end marked "U", and the patient end refers generally to the end marked "P." As used herein, the term "glass" should be understood to include other similarly chemically inert materials suitable for use in a pharmaceutical grade application that would normally require type I borosilicate glass, quartz, including but not limited to certain non-reactive polymers such as cyclic olefin copolymers (COC), cyclic olefin polymers (COP), and the like used in pharmaceutical prefillable syringes. These syringes may involve additional treatments such removal of subvisible particulates to make them appropriate for ophthalmic drugs. Plastic also refers to polymers such as polypropylene, polycarbonate and the like used in hypodermic syringes. The term "elastomer," "elastomeric" or "elastomeric materials commonly used in the manufacture of plunger seals in syringes. This also includes plunger seals that may be coated to afford chemical inertness for certain pharmaceutical applications. "Fluid" refers primarily to water, but can also refer to solutions such as polyethylene glycol, solids suspended in solution, immiscible substances in solution and refers to Newtonian as well as non-Newtonian liquids; all of these are injectable using a syringe. A system with needle safety can refer to safety implemented either with a retractable needle mechanism or an external sheath/cover for the needle. When a needle used is for administration, the needle is typically made of stainless steel; needles also include microneedles and microneedle arrays. Needle size used could range from 21G through 40G in diameter and up to 1" in length. Administration could be subcutaneous, intravenous, intradermal, intravitreal, intraocular, suprachoroidal, sub-conjunctival, intra-tumoral, intracellular, topical, etc.

Embodiments of a mechanism to set and deliver an accurate, precise injectable dose and embodiments of drug delivery syringe(s) that could incorporate such mechanisms are described below. Such devices can be safe and easy to use, aesthetically appealing, and designed per ergonomic considerations of their users, which may include researchers, veterinary health practitioners, and other clinical practitioners. Ergonomic features may be included that enable activation, operation, and disposal of devices with minimal or no training. Embodiments of dose control mechanisms, fluid delivery syringes, and respective components are described further herein with reference to the accompanying figures.

Figure 2:
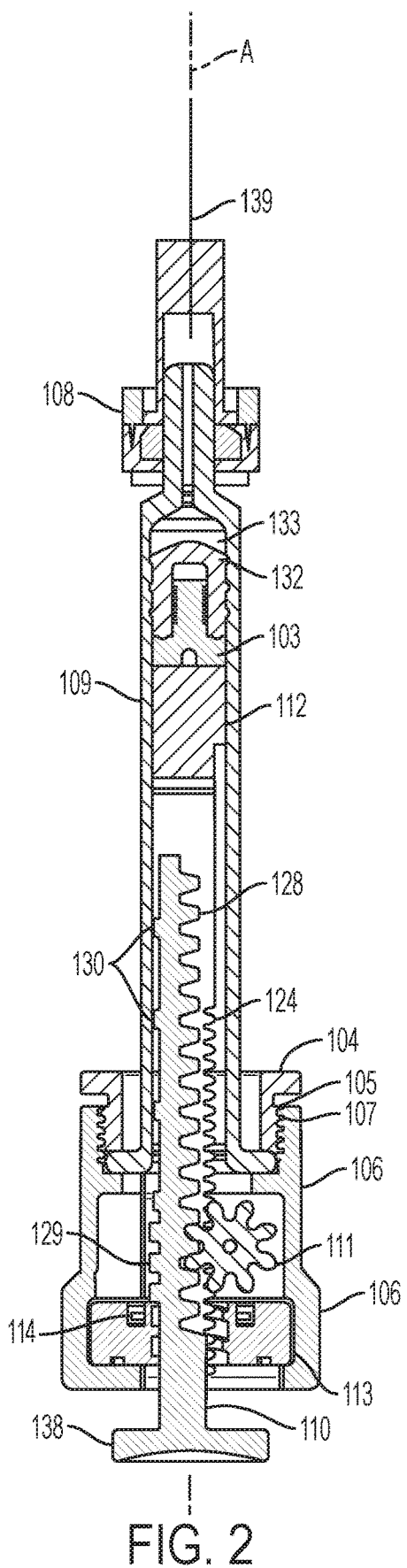
FIG. 2 is a cross-sectional view of the system of FIG. 1.
Figure 3:
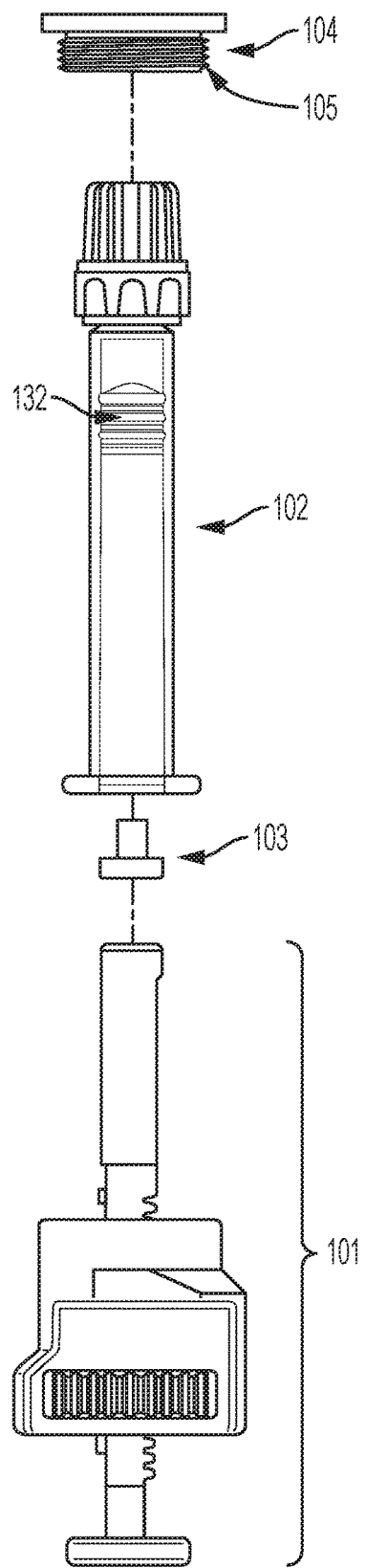
FIG. 3 is an exploded view of the system of FIG. 1.

FIGS. 1-3 illustrate a syringe-based system 100 incorporating an accurate, precise dose delivery mechanism, according to a first embodiment. System 100 includes plunger rod subassembly 101, prefillable syringe 102, plunger seal adapter 103, and cover 104. Cover 104 is affixed to plunger rod subassembly 101 by the engagement of external threads 105 on cover 104 with internal threads 107 on the barrel opening end of housing 106. In other embodiments, cover 104 may be affixed to housing 106 using other means, including press fitting, snap-on features, fasteners, etc. According to some embodiments, the prefillable syringe may include a luer lock adapter 108 or a staked/pre-attached needle. In some embodiments, a cartridge may be used instead of a syringe. In some embodiments, a delivery adapter may be used that enables topical delivery or intranasal delivery. The prefillable syringe 102 may be sprayed on the inside of the syringe barrel 109 with silicone oil such as Dow Corning 360 to provide lubrication. Alternatively, a siliconization emulsion such as Dow CORNING 365 may be sprayed. The syringes may be baked at a high temperature to bake the silicone onto the inside of the syringe barrel 109.

Figure 4:
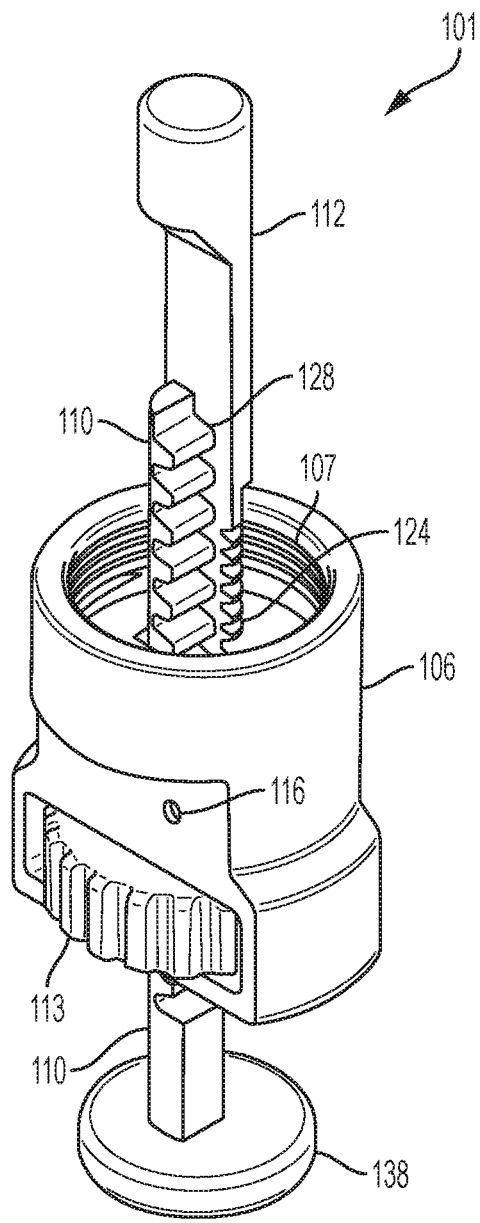
FIG. 4 is a perspective view of a dosing mechanism, according to an embodiment.

According to some embodiments, the plunger rod subassembly 101, an embodiment of which is shown separately in FIG. 4, includes a multi-component plunger rod that includes plunger rod 110 and drive rod 112. Plunger rod subassembly 101 also includes housing 106, gear 111, drive rod 112, thumb nut 113, and a spring 114.

Figure 5:
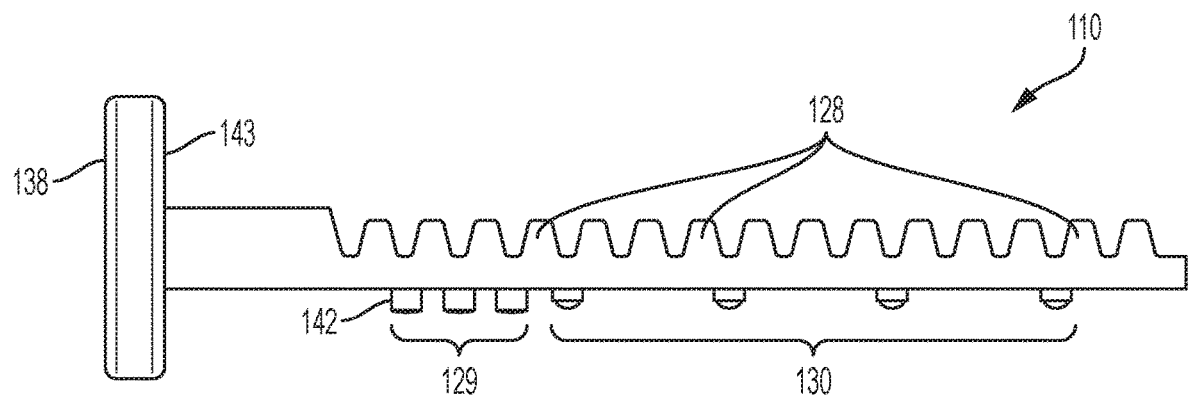
FIG. 5 is a side view of a plunger rod, according to an embodiment.
Figure 6:
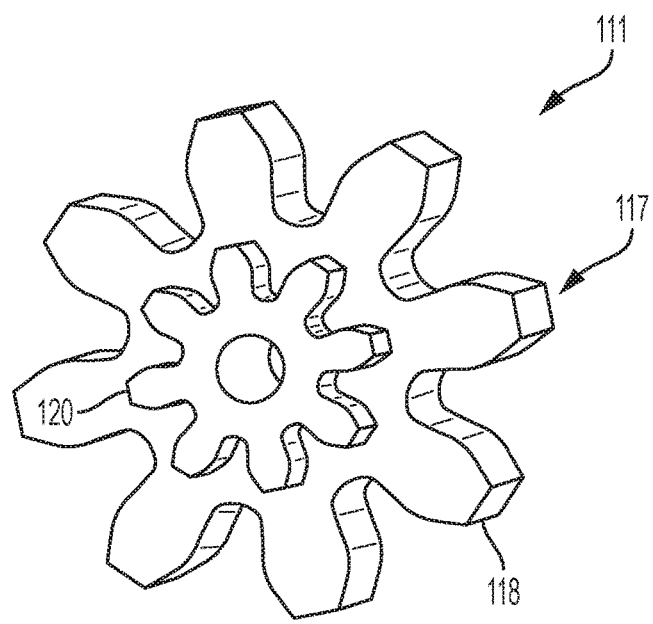
FIG. 6 is a perspective view of a compound gear, according to an embodiment.

Plunger rod 110 includes a set of linear gear teeth 128 along a portion of its length (FIG. 5). Teeth 128 mesh with a first set of larger pitch gear teeth 118 on gear 111. Gear 111 is pinned to the housing such that it can rotate but it cannot translate. Thus, linear movement of plunger rod 110 causes gear 111 to rotate. Gear 111 is a compound gear (FIG. 6) with a second set of smaller pitch gear teeth 120 that engage with a set of linear gear teeth 124 on drive rod 112. Thus, rotation of gear 111 causes axial advancement of drive rod 112 in the patient "P" direction, pushing the non-patient surface of the plunger adapter 136. This, in turn, pushes the filled fluid 133, dispensing it through the tip of the needle 139 (or other component). Due to the difference in pitch between the two sets of teeth of the compound gear, the drive rod 112 advances a smaller amount than the plunger rod 110 and a mechanical advantage is provided such that less user force is required than would be required to directly push plunger seal 132. In other embodiments, the configuration of gear 111 may be reversed such that the smaller pitch gear teeth interface with the plunger rod and the larger pitch gear teeth interface with the drive rod.

Figure 7A:
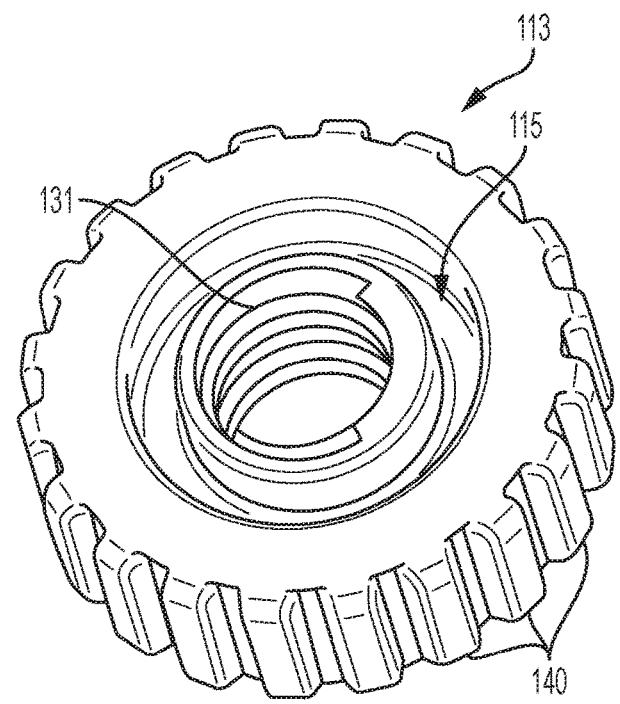
FIGS. 7A and 7B are perspective and cross-sectional views, respectively, of a thumb nut, according to an embodiment.
Figure 7B:
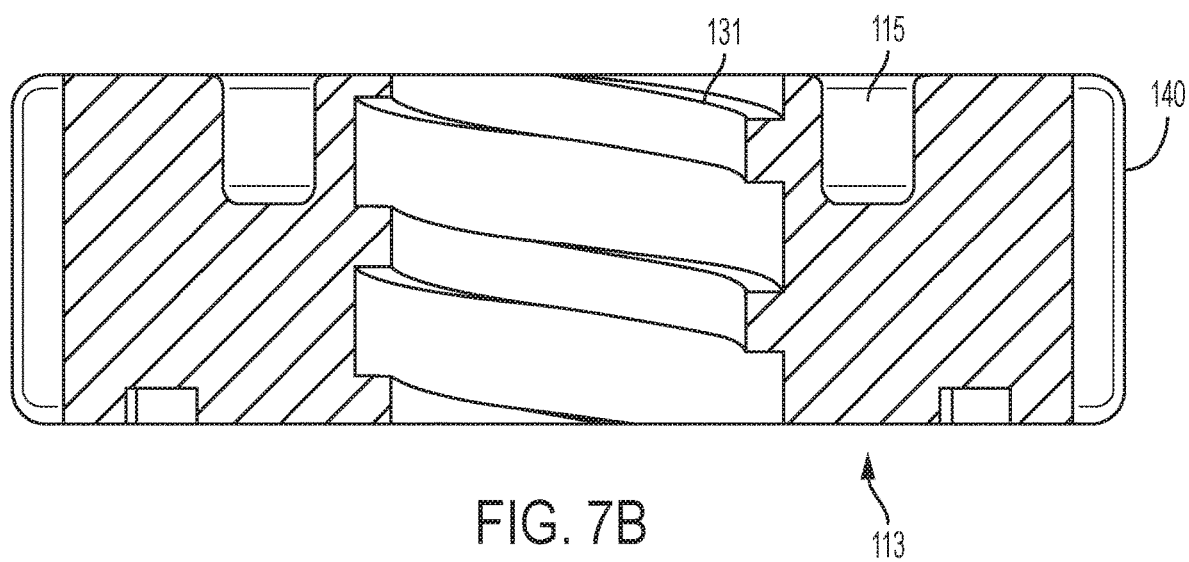

Plunger rod 110 also includes a plurality of dosing pegs 129 that engage with an internal thread 131 of thumb nut 113 (FIGS. 7A-7B). At least a portion of plunger rod 110 may include a non-circular cross-section that fits within a complimentary aperture in the housing, which prevents rotation of plunger rod 110. With plunger rod 110 constrained against rotation, the rotation of thumb nut 113 causes axial movement of plunger rod 110. The engagement of dosing pegs 129 with internal thread 131 also prevents a user from pushing plunger rod 110 to axially advance plunger rod 110. Continued axial advancement of the plunger rod 110 via turning of thumb nut 113 will result in a rearmost dosing peg 142 (the dosing peg nearest the user end of the plunger rod 110) escaping the internal thread 131 of thumb nut 113. Once it has escaped, the thumb nut 113 no longer prevents a user from directly advancing plunger rod 110 by pushing on plunger rod 110. According to some embodiments, lugs 130 are provided on the plunger rod 110 to help maintain orientation of the plunger rod 110 inside the syringe barrel 109.

Assembly of the plunger rod subassembly 101 may include placing the spring 114 in seat 115, which is cavity in thumb nut 113. The gear 111 may be attached to the housing 106 using a cylindrical pin 116 such that the back surface 117 of the larger pitch teeth 118 abut housing 106. There may be interference between the pin 116 and two holes 122, 123 in the housing 106 ensuring that there is no rotational slip. The gear 111 may rotate freely about the axis of the pin 116.

Figure 8A:
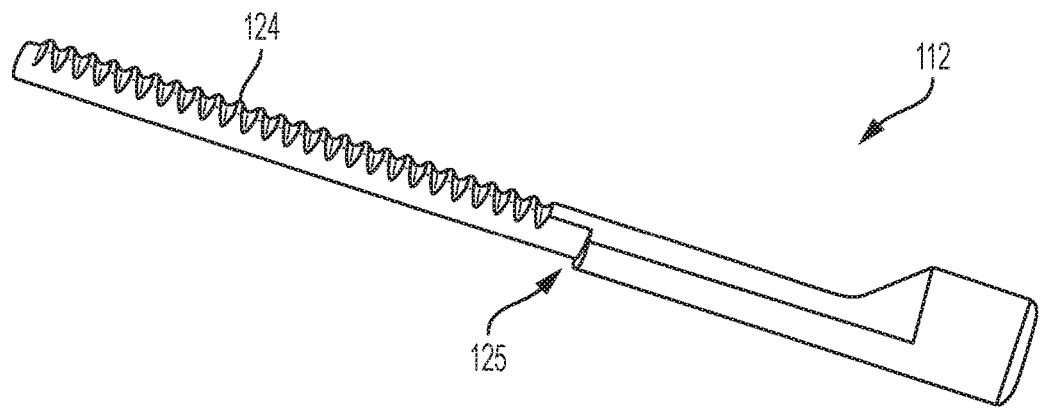
FIGS. 8A and 8B are perspective and side views, respectively, of a drive rod, according to an embodiment.
Figure 8B:
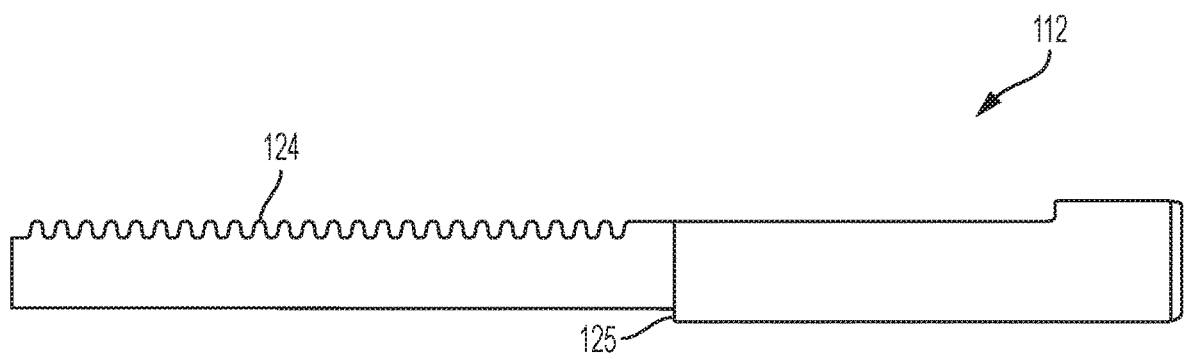
Figure 9A:
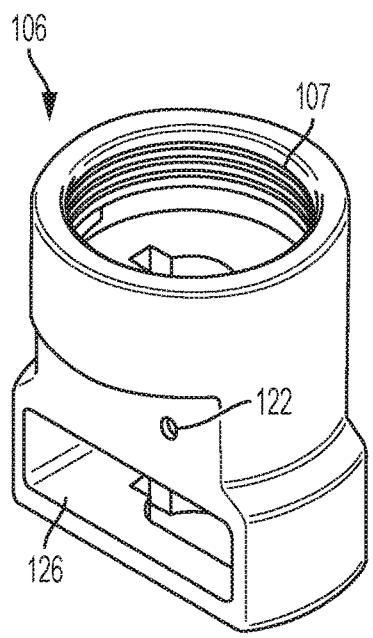
FIGS. 9A-9D are perspective, perspective cross-sectional, cross-sectional, and bottom views of a housing, according to one embodiment.
Figure 9C:
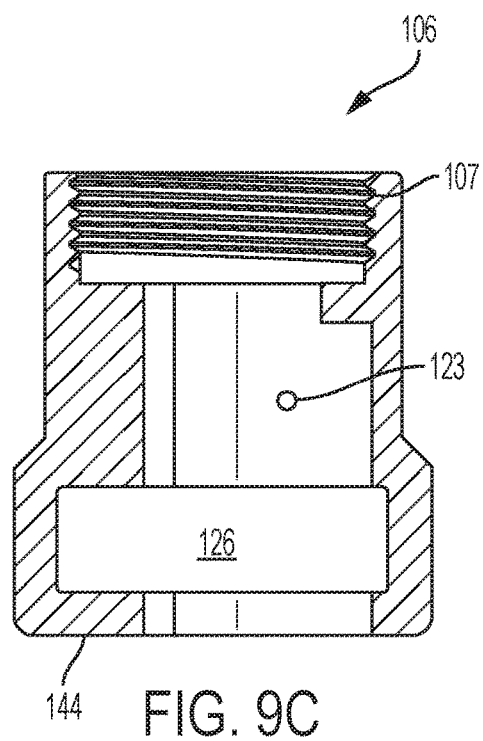
Figure 9B:
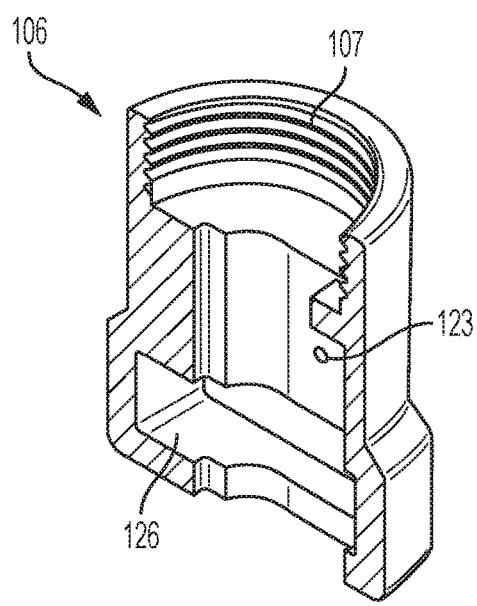
Figure 9D:
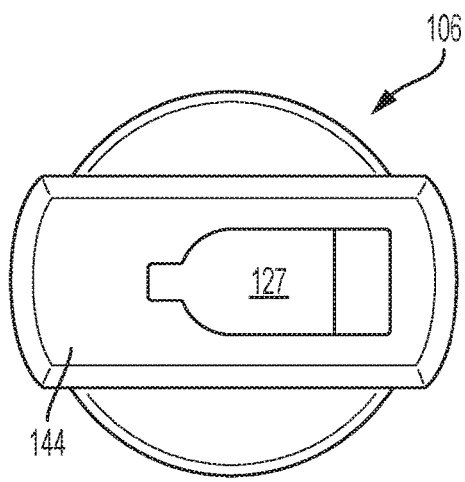

Spring 114 inside the thumb nut 113 may then be slid inside housing 106 as an assembly through opening 126 such that the open side of the spring 114 is facing the patient end "P" of the system. Spring 114 may preload the thumb nut 113 against the housing to reduce any axial play that may arise from component tolerances. The drive rod 112 may be inserted from the patient end P such that teeth 124 on drive rod 112 interact with smaller pitch teeth 120. The drive rod 112 may be pushed all the way until a hard stop when the shoulder 125 on the drive rod (FIGS. 8A and 8B) touches the surface of the housing 106. The plunger rod 110 may then be inserted through the dorsal cavity 127 (see FIG. 9A-9D) in the housing 106 such that teeth 128 are pointed away from the user end "U" and in a manner that they interact with the larger pitch teeth 118. The pegs or lugs 129 on the plunger rod 110 interfere with the internal thread 131 on the thumb nut 113 such that rotation of the thumb nut 113 in one direction advances the plunger rod 110 in the direction of the patient end "P". The shape of dorsal cavity 127 of the housing 106 is matched with the cross-section of the plunger rod 110, and is designed such that it would prevent any rotation of the plunger rod 110. The plunger rod subassembly 101 is now assembled.

To assemble a prefilled syringe, according to some embodiments, the fluid 133 may be filled from the non-patient end of the syringe and then a substantially elastomeric plunger seal 132 is inserted from the non-patient end towards the patient end. This is now a filled syringe. A plunger adapter 136 may be screwed into the back of the plunger seal 132 with matching, complementary threads 137. In order to attach the plunger rod subassembly 101 to this prefilled syringe, the patient end "P" of the plunger rod subassembly 101 may be inserted from the user end "U" of prefilled syringe inside the syringe barrel 109. The cover 104 with its threads 105 oriented towards the user end "U" may then be slid across the length of the syringe barrel 109 until it mates with the threads 107 on the housing. The cover may be turned until tightened. The accurate, precise dosing syringe-based system 100 is now completely assembled. This assembled system is ready for use by the user, ready for secondary packaging, and/or ready for terminal sterilization as required for certain applications.

In this embodiment, when ready to use, the user can attach a needle 139 by twisting and turning on the luer lock adapter 108 of the syringe. By pointing the patient end "P" of the syringe upwards, the user rotates thumb nut 113 to set the dose. Striated features 140 may be provided on the outer curved surface of the thumb nut 113 to allow for better grip and tactile feel. Markings 141 on the dorsal surface of the thumb nut 113 may provide a visual cue to the user of the direction of rotation of the thumb nut 113 for dose setting. As the thumb nut 113 is rotated, the internal threads 131 act as a guide for pegs or lugs 129 on the plunger rod 110, thereby advancing the plunger rod 110.

Figure 11A:
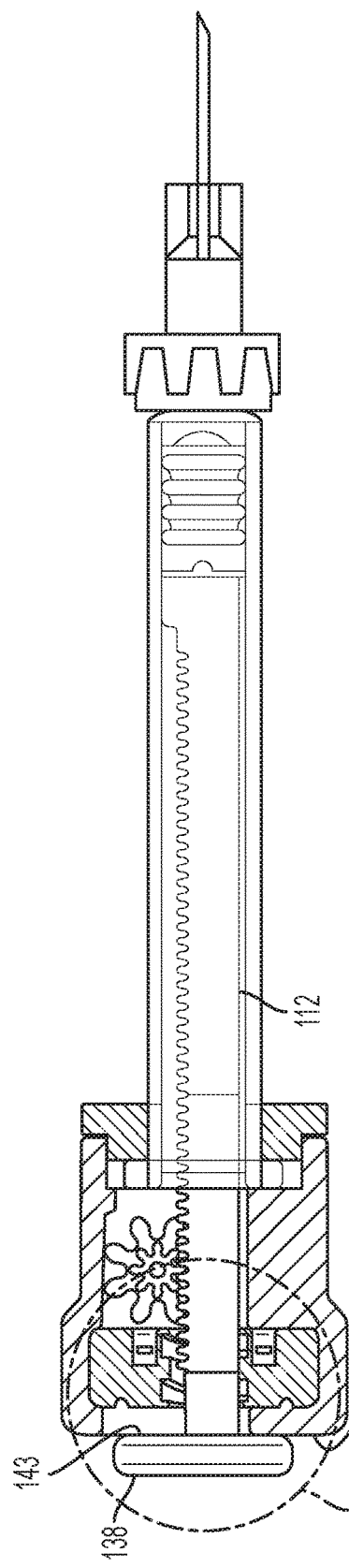
FIGS. 11A and 11B are cross-sectional views illustrating the dose delivered configuration of the system of FIGS. 10A and 10B.
Figure 11B:
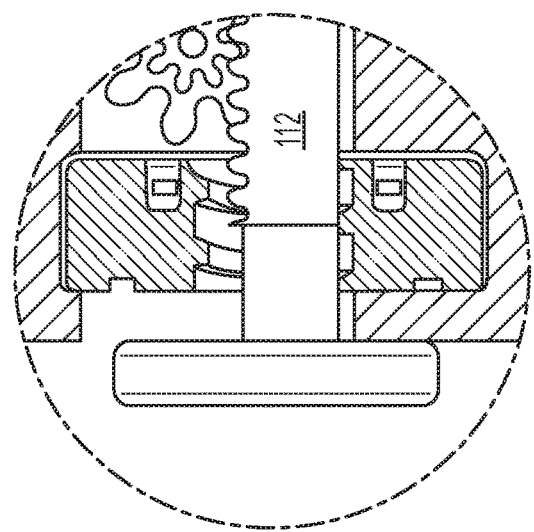
Figure 12:
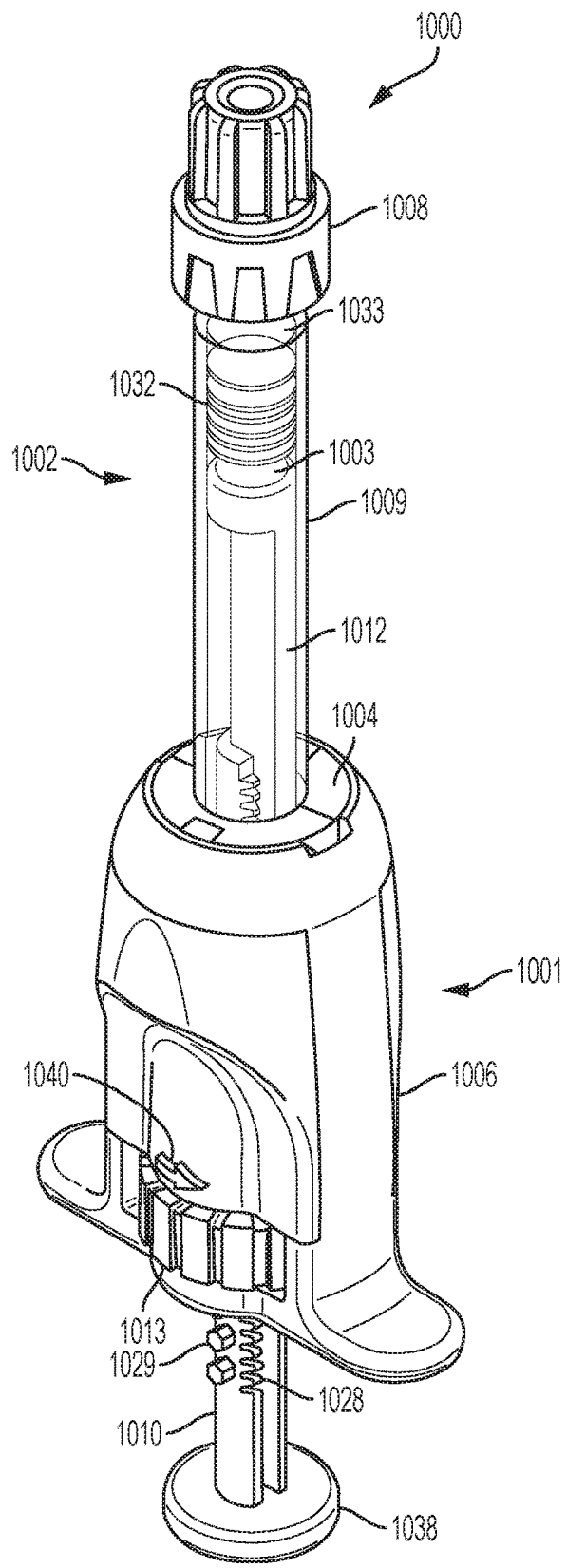
FIG. 12 is a perspective view of a dosing syringe system according to a second embodiment.
Figure 13:
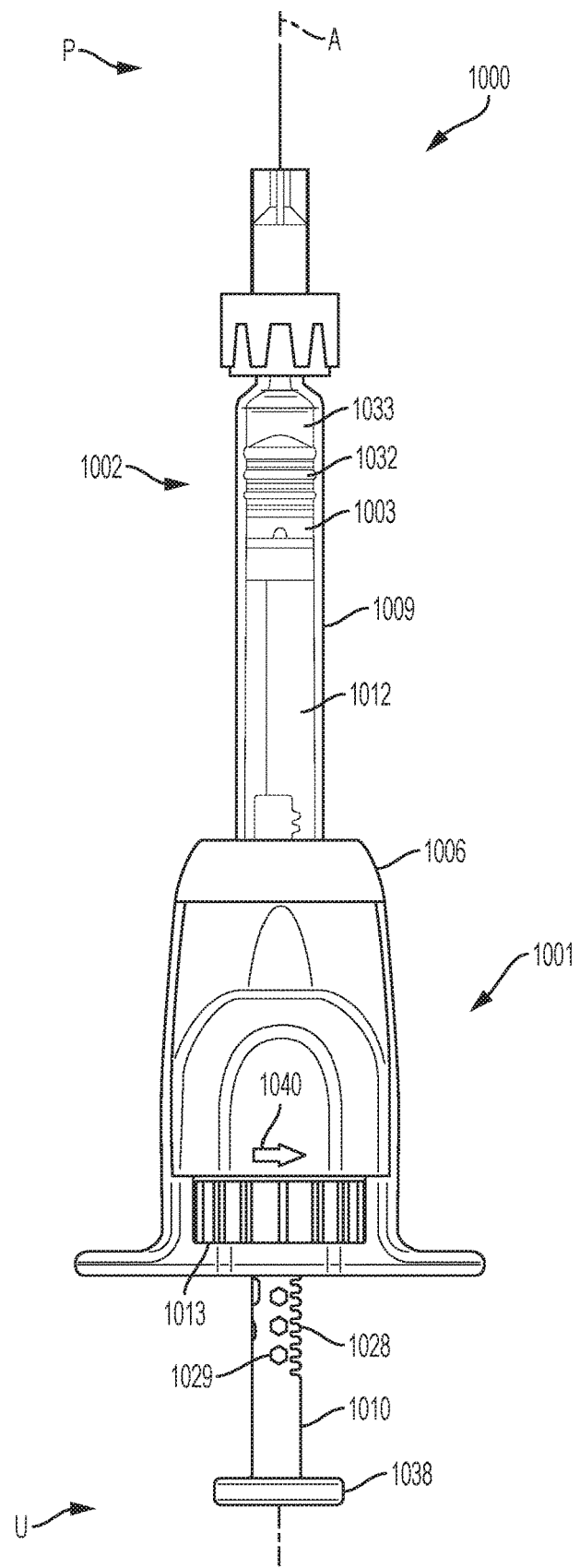
FIG. 13 is a side view of the system of FIG. 12.
Figure 14:
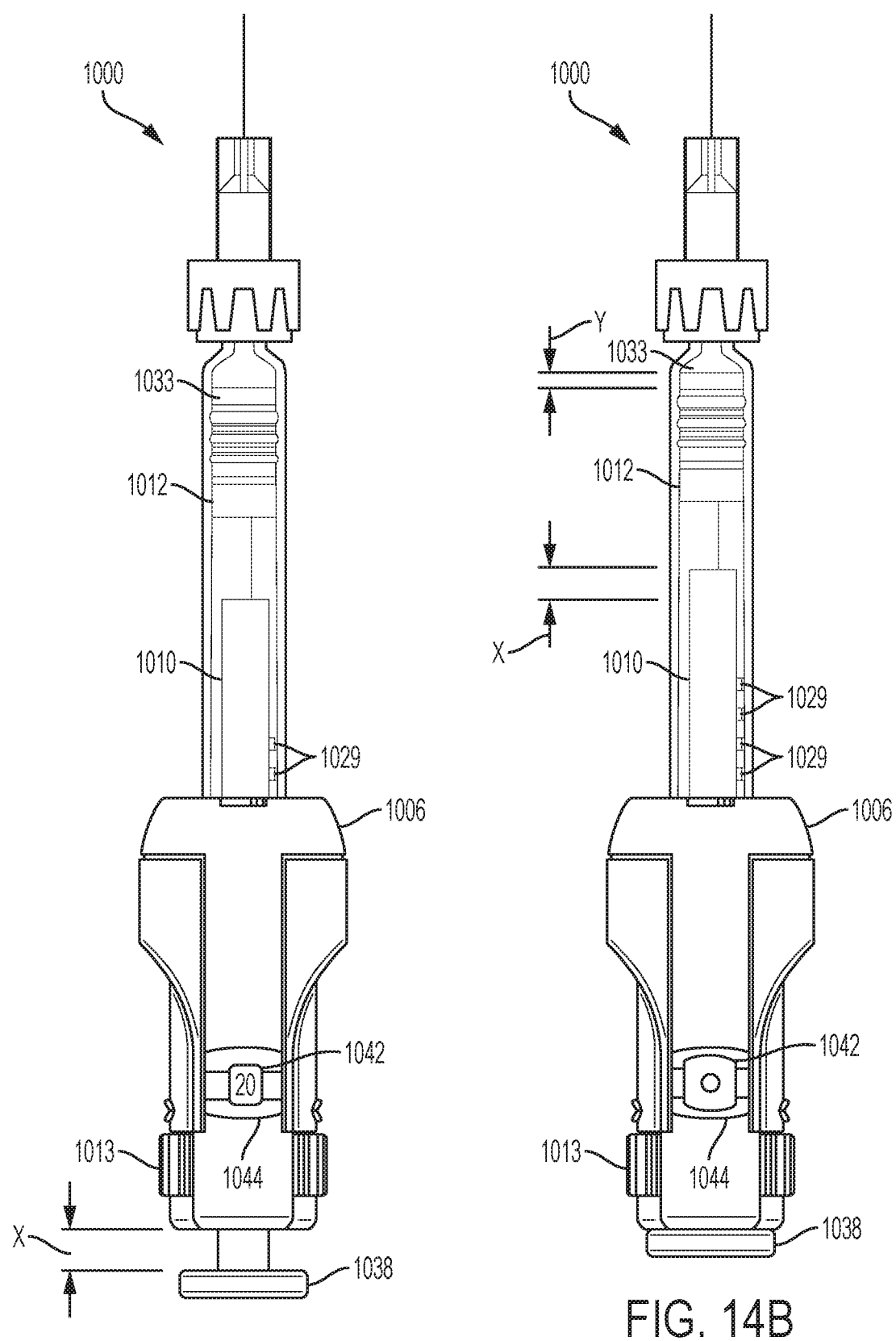
FIGS. 14A and 14B are side views of the dosing system of FIG. 12 in a dose set configuration and a dose delivered configuration, respectively.

As the user continues to rotate the thumb nut 113, the plunger rod 110 is axially advanced in direction "P" until the dose set peg 142 (the last peg) exits from the thread 131 inside the thumb nut 113. After this point, subsequent rotation of the thumb nut 113 does not cause any axial translation of the plunger rod 110, and thus, does not cause any more fluid to be dispensed. The dose is now "set." This configuration is illustrated in FIGS. 10A and 10B. The user then inserts the needle into the target site for delivery and pushes the thumb rest 138 on the plunger rod 110 until the underside 143 of thumb rest 138 contacts the surface 144 of the housing 106. This configuration is illustrated in FIGS. 11A and 11B. An accurate, precise dose is now delivered and system 100 can be safely discarded.

FIGS. 12-15 illustrate a syringe-based system 1000 incorporating an accurate, precise dose delivery mechanism, according to a second embodiment. System 1000 includes plunger rod subassembly 1001 coupled to a prefillable syringe 1002. Prefillable syringe 1002 may include luer lock adapter 1008 and a plunger seal 1032. Prefillable syringe 1002 is shown with a cap in FIG. 12 and with a needle in FIG. 13, for illustration purposes. A plunger seal adapter 1003 may be provided in the prefillable syringe 1002 to serve as the interface between the plunger seal 1032 and the plunger rod subassembly 1001.

The plunger rod subassembly 1001 is affixed to the user end of the prefillable syringe. The plunger rod subassembly 1001 includes drive rod 1012, which drives the plunger seal 1032 (e.g., via plunger seal adapter 1003) during dose delivery, and plunger rod 1010, which is driven by a user press during dose delivery. Plunger rod subassembly 1001 also includes housing 1006, housing clip 1004 and thumb nut 1013. The operation of system 1000 is similar to that of system 100 in that a user rotates thumb nut 1013 to set the dose and then presses on plunger rod 1010 to deliver the dose. Housing 1006 may include an indicator 1040 for indicating the direction of rotation of thumb nut 1013 for dose setting. Rotation of thumb nut 1013 causes plunger rod 1010 to advance via the engagement of an internal thread on thumb nut 1013 with dosing lugs 1029 on the plunger rod 1010. Advancement of plunger rod 1010 causes advancement of drive rod 1012 via a gear train that couples the movements of the plunger rod and the drive rod. Once the dosing lugs 1029 have cleared the internal thread on the thumb nut 1013, the dose is set, and a user press on the user end of plunger rod 1010 causes plunger rod 1010 to fully advance, which in turn, causes drive rod 1012 to push plunger seal 1032 to expel the set dose.

FIG. 14A shows system 1000 in the dose set configuration. The plunger rod 1010 has advanced within housing 1006 to the point that the dosing lugs 1029 have cleared the internal thread on the thumb nut 1013. In the illustrated embodiment, a dose indication 1042 ("20") can be seen through a window 1044 on the side of housing 1006 to indicate that the dose has been set and/or the amount of the dose that has been set. FIG. 14B shows system 1000 in the dose delivered configuration. A user press on the thumb rest 1038 of plunger rod 1010 has advanced plunger rod 1010 to its fully depressed position, against housing 1006. The patient end of plunger rod 1010 has advanced within syringe barrel 1009. The drive rod 1012, plunger seal adapter 1003, and plunger seal 1032 have also advanced within syringe barrel 1009 to a lesser degree than plunger rod 1010 due to the gear reduction of the gear train, as will be discussed in more detail below. Thus, the plunger rod travel "X" is greater than the drive rod travel "Y". In the embodiment shown, the dose indication 1042 shown through window 1044 is "0" to indicate that the set dose has been fully dispensed.

Figure 15:
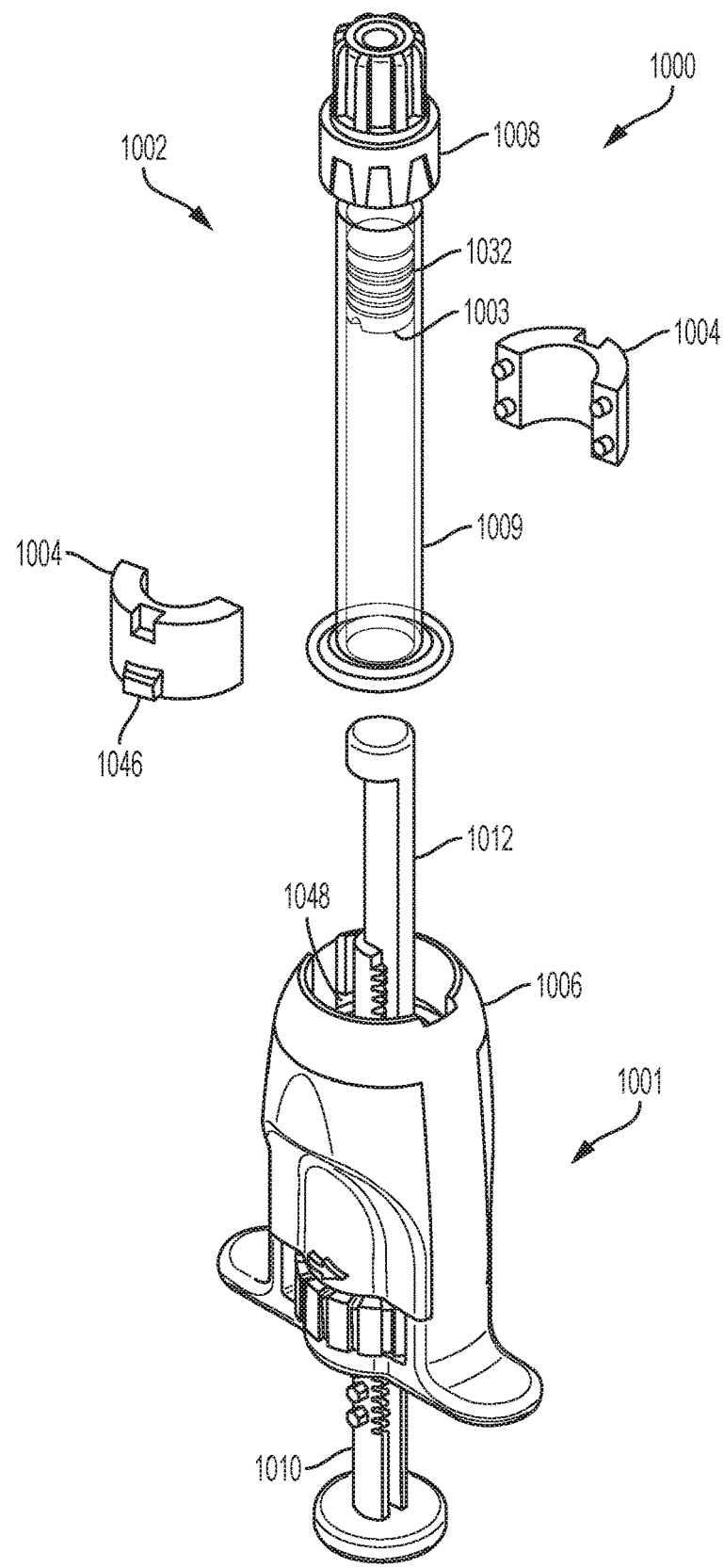
FIG. 15 is a perspective view illustrating the coupling of a dosing mechanism to a syringe barrel, according to an embodiment.
Figure 16A:
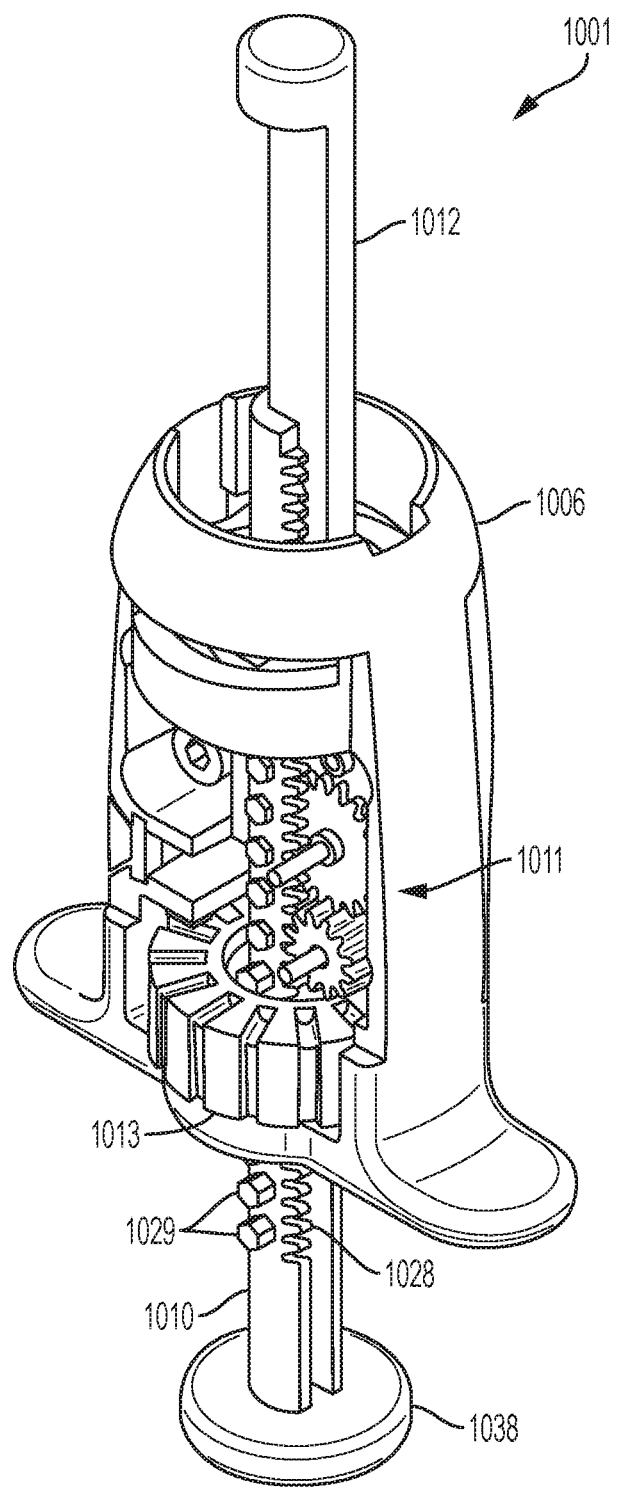
FIGS. 16A and 16B are perspective and side views, respectively, illustrating a gear train, according to an embodiment.
Figure 16B:
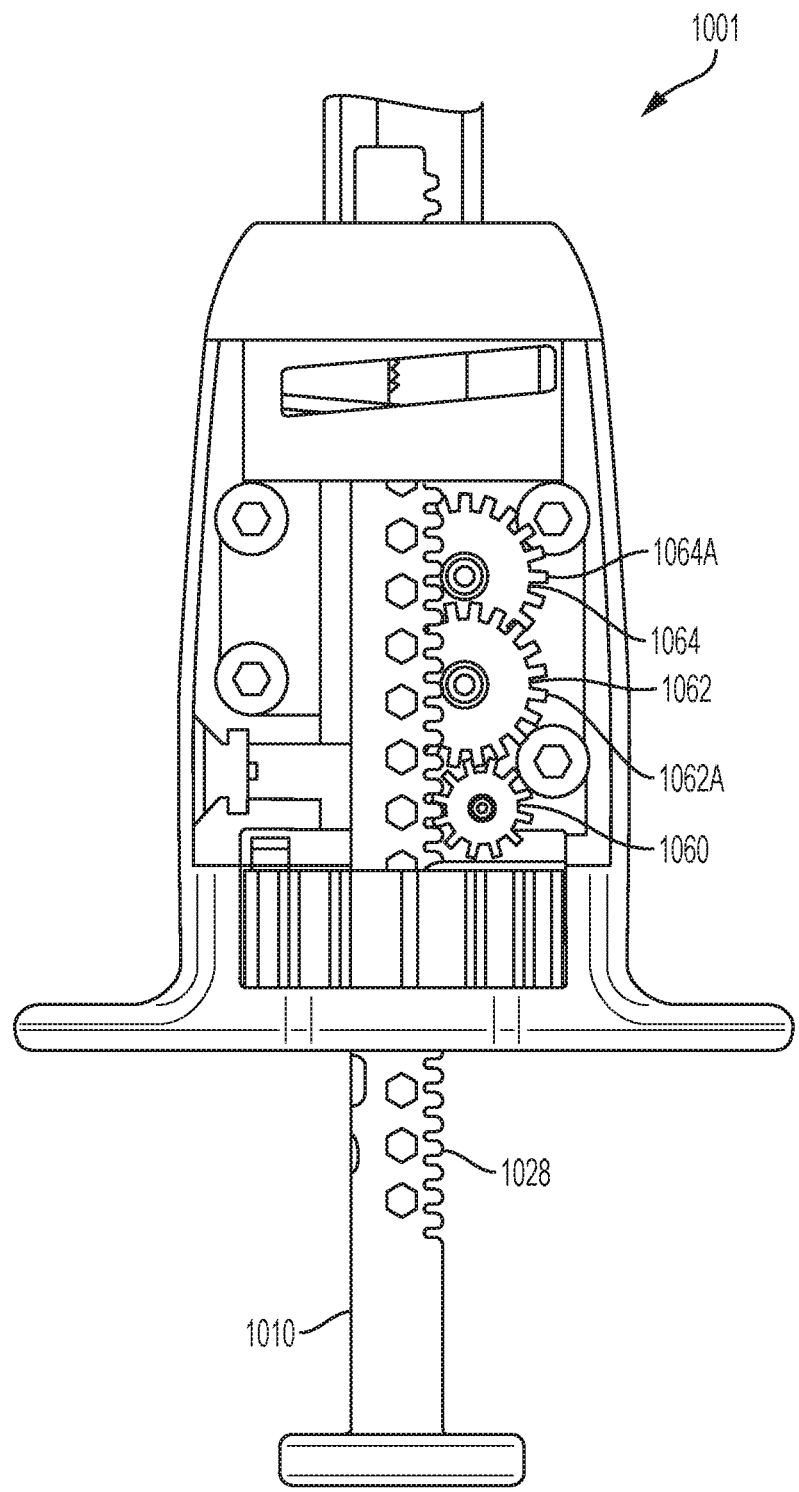

FIG. 15 illustrates the assembly of plunger rod subassembly 1001 onto syringe barrel 1009, according to some embodiments. The patient end of the plunger rod subassembly 1001 may be inserted from the user end of syringe barrel 1009. Clip 1004 is positioned around syringe barrel 1009. Clip 1004 may be formed of two pieces that may register to one another with one or more pegs or other registering features. In some embodiments, the pieces snap together, for example, via an interference fit of registering features. The clip pieces may be screwed together, glued together, or otherwise affixed to one another using any suitable method. In some embodiments, clip 1004 is a unitary piece, such as cover 104 of system 100. Once clip 1004 is positioned around syringe barrel 1009, clip 1004 is slid toward the user end of syringe barrel 1009 to interface with the patent end of housing 1006. Clip 1004 may include one or more tabs 1046 that engage with an inner-facing groove 1048 in the patient end of housing 1006 such that turning clip 1004 once the tabs 1046 are engaged in groove 1048 (for example, a quarter turn) locks the housing 1006, syringe barrel 1009, and clip 1004 together. In some embodiments, clip 1004 includes an external thread that mates with an internal thread on the housing (for example, similar to system 100 described above). In some embodiments, clip 1004 includes one or more recesses for insertion of a tool, such as a spanner wrench, to turn clip 1004 in housing 1006. In some embodiments, compliance in one or more of clip 1004 and housing 1006 (for example, compliance of tabs 1046) results in preloading of the housing, cover, and syringe barrel once clip 1004 is tightened into housing 1006, which eliminates free play between the components. In some embodiments, a compliance component (such as a wave spring, coil spring, gasket, etc.) is included to preload the syringe barrel-to-housing engagement FIGS. 16A and 16B show a gear train 1011 that couples plunger rod 1010 and drive rod 1012, according to some embodiments. The gear train 1011 includes rotor gear 1060, lower force gear 1062, and higher force gear 1064. Lower force gear 1062 and higher force gear 1064 are both compound gears, each having two sets of gear teeth. Rotor gear 1060 is pinned to the housing through its axis of rotation and includes teeth that engage a set of teeth on plunger rod 1010 such that linear movement of plunger rod 1010 causes rotational movement of rotor gear 1060. The teeth on rotor gear 1060 also engage a first set of teeth 1062A on lower force gear 1062, which is also pinned to the housing, such that rotation of rotor gear 1060 causes rotation of lower force gear 1062. Lower force gear 1062 includes a second set of gear teeth 1062B on the other side (see FIG. 17A). The second set of gear teeth 1062B engage a first set of gear teeth 1064A on higher force gear 1064, which is pinned to housing 1006, such that rotation of lower force gear 1062 causes rotation of higher force gear 1064. Higher force gear 1064 includes a second set of gear teeth 1064B on the other side (see FIG. 17A). The second set of gear teeth 1064B engage a set of linear gear teeth 1024 on drive rod 1012 such that rotation of higher force gear 1064 causes linear movement of drive rod 1012. Thus, gear train 1011 converts linear motion of plunger rod 1010 to linear motion of drive rod 1012.

The gear train may be configured to provide a stroke reduction of the drive rod relative to the plunger rod and a mechanical advantage through the configuration of the gears. As illustrated, the pitch of the first set of teeth 1062A on lower force gear 1062 may be greater than the pitch of the teeth on rotor gear 1060 such that lower force gear 1062 rotates less than rotor gear 1060. The pitch of the second set of gear teeth 1062B may be less than the pitch of the first set of teeth 1062A. The pitch of the first set of gear teeth 1064A on higher force gear 1064 may be greater than the pitch of the second set of teeth 1062A and the pitch of the second set of gear teeth 1064B on higher force gear 1064 may be less than that of the first set of gear teeth 1064A. This configuration results in the drive rod 1012 moving a fraction of the amount that plunger rod 1010 moves and results in a mechanical advantage such that the force required to depress the plunger rod 1010 is less than it would be if no gear train were provided.

One of skill in the art will readily understand that a gear train may be configured with any suitable combination of gears to achieve design requirements, such as gear reduction, mechanical advantage, compactness, etc. For example, according to some embodiments, the gear train may include just a single compound gear, such as gear 101 of system 100 described above. A gear train may include two gears or four or more gears. Any of the gears may include just a single tooth pitch or may include two or more tooth pitches. A gear train may include idler gears, epicyclic gears, or any other suitable gears or gear arrangements. Further, embodiments may be configured to reverse the gear reduction described above such that axial movement of the drive rod is greater than axial movement of the plunger rod.

Figure 17A:
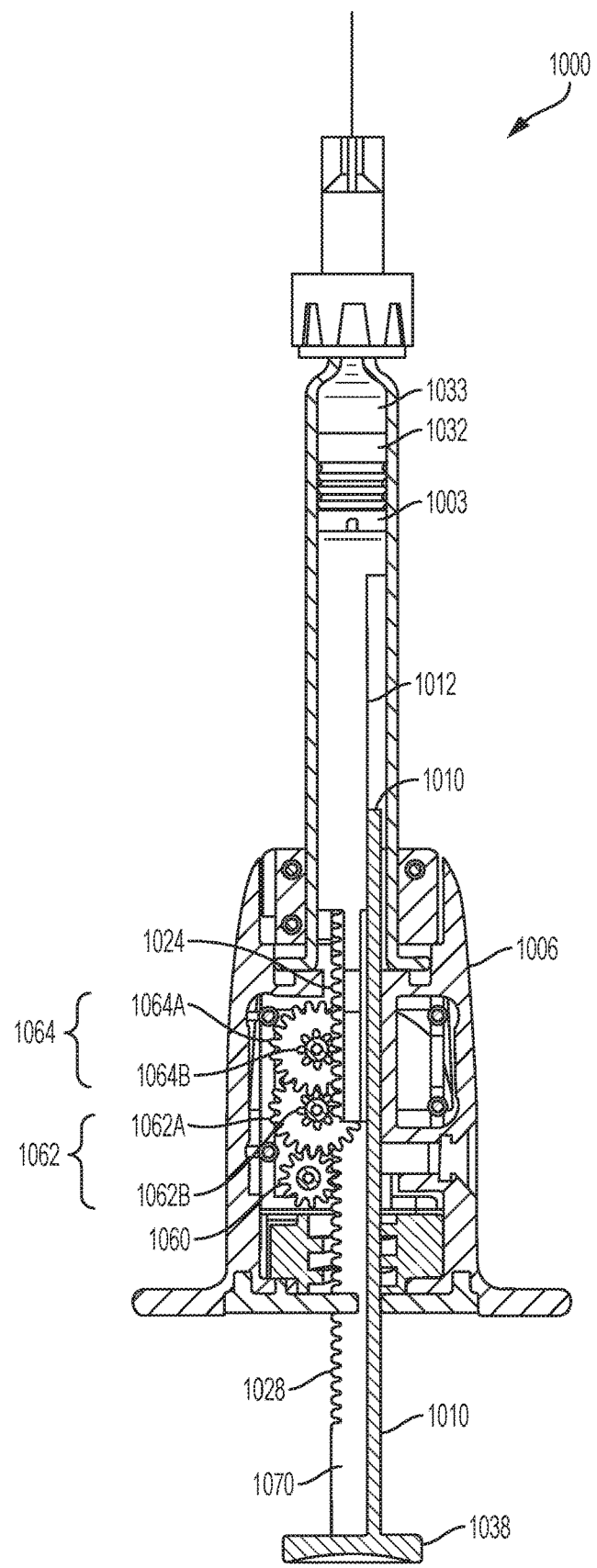
FIGS. 17A-17C are cross-sectional views illustrating a dose setting and dose delivery process.
Figure 17B:
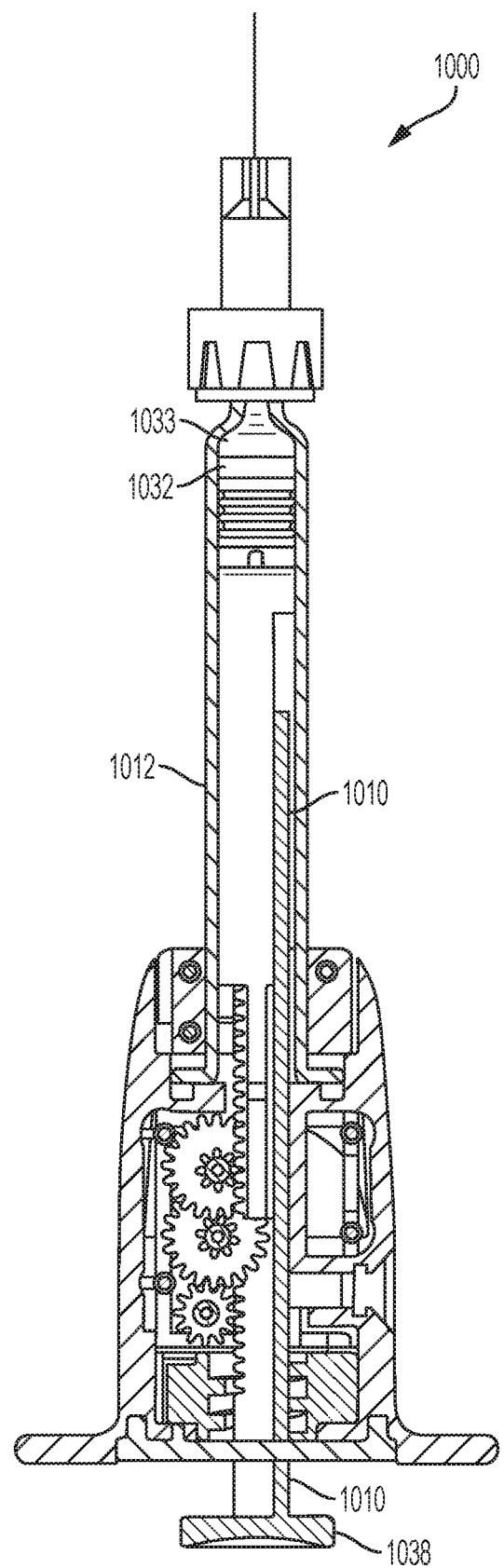
Figure 17C:
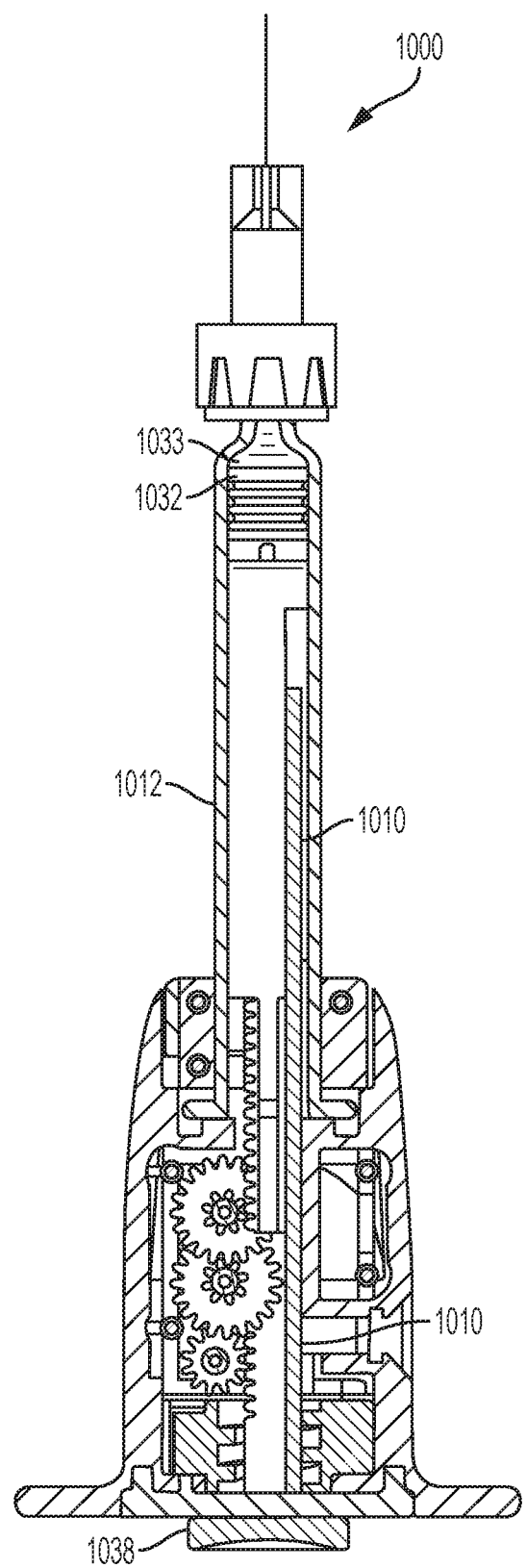

FIG. 17A-C are cross-sectional views illustrating the dose setting and dose delivery configurations of system 1000, according to some embodiments. FIG. 17A shows system 1000 in an "as-delivered" state, prior to the dose being set. In this state, the plunger rod 1010 cannot be pushed in by a user press because of the engagement of at least one dosing lug 1029 on plunger rod 1010 with the internal thread of thumb nut 1013. To set the dose, the user turns thumb nut 1013 in the dose setting direction (for example, as indicated by indicator 1040), causing dosing lugs 1029 (and, thus, plunger rod 1010) to be advanced by the internal thread of thumb nut 1013.

System 1000 is shown in the dose set state in FIG. 17B. As shown, plunger rod 1010 has moved toward the patient end but the thumb rest 1038 is still spaced from the housing. Through action of the gear train 1011, the drive rod 1012 has advanced within the syringe barrel 1009, though to a lesser degree due to the gear reduction of the gear train 1011 described above. Although not shown in FIG. 17B, all of the dosing lugs 1029 have escaped the internal thread of thumb nut 1013 such that further turning of thumb nut 1013 in the dose setting direction causes no further advancement of plunger rod 1010. In some embodiments, thumb nut 1013 includes one or more stops that engage with dosing lugs 1029 to prevent further turning of thumb nut 1013 in the dose setting direction, as will be described in more detail below, which can provide an indication to the user that the dose is set and can provide precise positioning of the plunger rod 1010. The system 1000 is now ready for dispensing the set dose. FIG. 17C illustrates system 1000 in the dispensed configuration. Plunger rod 1010 has been advance fully to the point that its thumb rest 1038 abuts the user end of housing 1006. As illustrated, the drive rod 1012, plunger seal adapter 1003, and plunger seal 1032 have advanced within syringe barrel 1009, expelling the set dose. As is readily apparent, the dosage delivered is proportional to the stroke of the drive rod 1010 during the dose delivery process. The stroke of the drive rod 1012 during dose delivery is controlled by the gear train configuration and by the distance between the rearmost dosing lugs 1029 and the underside of the thumb rest 1038, which determines the dose delivery stroke of the plunger rod. Thus, the drive rod stroke can be tailored for specific applications by the dosing lug configuration and the gear train configuration.

Figure 18C:
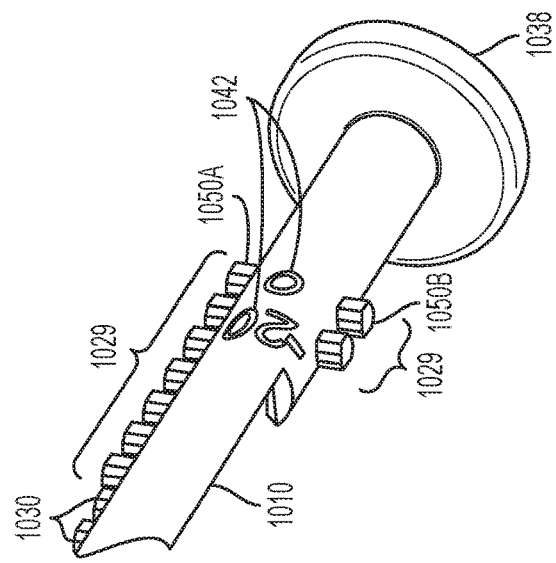
FIGS. 18A-18C illustrate the engagement of a thumb nut and plunger rod, according to an embodiment.
Figure 18B:
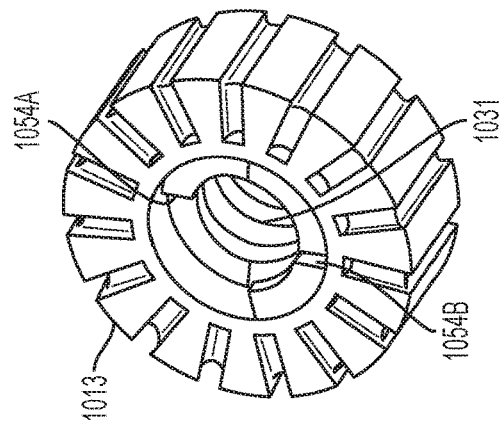
Figure 18A:
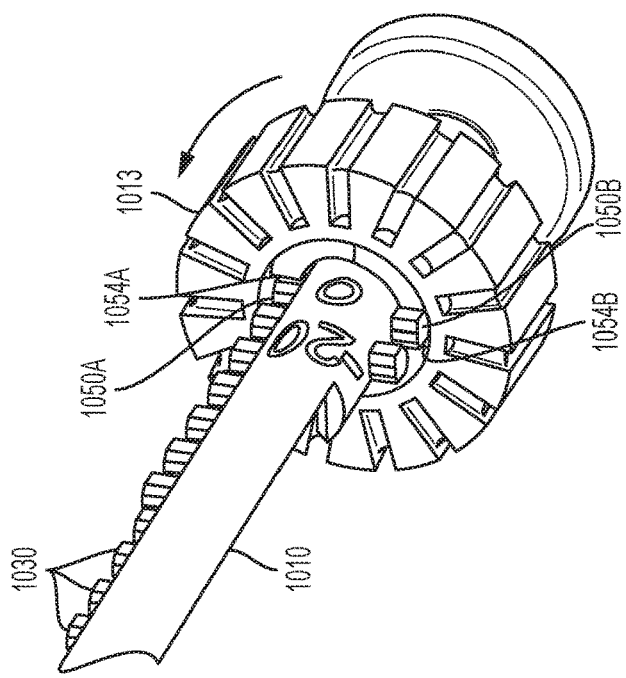

FIG. 18A-C illustrate the engagement between plunger rod 1010 and thumb nut 1013, according to some embodiments. FIG. 18A shows plunger rod 1010 and thumb nut 1013 in their relative positions when the system is in the dose set position. Plunger rod 1010 includes dosing lugs 1029 on two sides, which provides balanced loading on plunger rod 1010. In this embodiment, the second side includes fewer lugs than the first side. The rearmost lugs 1050A and 1050B have both emerged from the groove 1031 within thumb nut 1013 (FIG. 18B) and are abutting stops 1054A and 1054B at ends of groove 1031. These stops prevent thumb nut from being turned in the dose setting direction (the direction indicated by the arrow of FIG. 18A). By providing stops, the relative position of the lugs with respect to the thumb nut can be precisely controlled, allowing for precise control of the axial position of plunger rod 1010.

Plunger rod 1010, according to the illustrated embodiment, includes dosage indications 1042 on the side, which may show through window 1044 on the side of housing 1006 to indicate to the user conformation that the dose is set and that the dose delivery is complete. For example, once the dose is set (FIG. 17B), the number "20" (in this embodiment) may show through window 1044 to indicate to the user that the dose has been properly set. After the dose has been set and the plunger rod 1010 advances further within the housing 1006 during dosage delivery, the "20" marker moves axially out of window 1044 and the "0" marker moves axially into window 1044. Alignment of the "0" marker within window 1044 may indicate to the user that the dose has been completely delivered.

Figure 19:
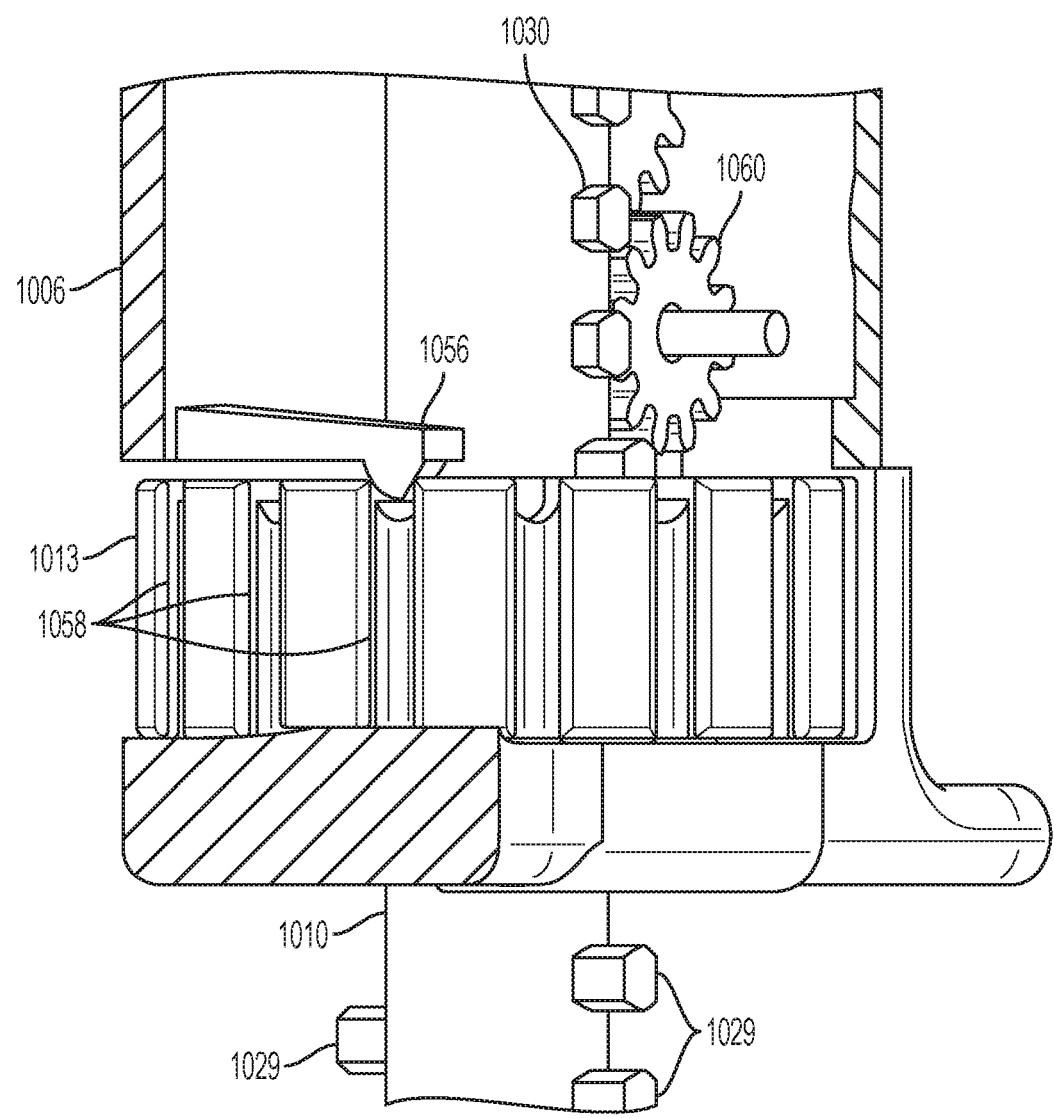
FIG. 19 illustrates a ratchet, according to an embodiment.

FIG. 19 illustrates a ratchet engagement between a pawl 1056 on the housing 1006 and grooves 1058 on the side of thumb nut 1013. This ratchet engagement serves dual purposes of preventing the thumb nut 1013 from being rotated in the direction opposite to the dose setting direction and providing an aural and/or tactile indication of the dose setting process. The ratchet engagement may also serve to urge thumb nut 1013 against the housing to control the axial positioning of the thumb nut. The pawl 1056 is configured such that it is urged into the grooves 1058 of the thumb nut 1013. One face of the pawl is configured such that the pawl rides out of a respective groove 1058 as the thumb nut 1013 is rotated in the dose setting direction. The pawl then snaps back into the next groove 1058, providing an aural and/or tactile indication of the movement of thumb nut 1013. In some embodiments, the opposite face of pawl 1056 is configured such that the pawl remains in the groove 1058 and prevents the thumb nut 1013 from being rotated in the counter direction such that the plunger rod 1010 can only be advanced in the dose-setting direction. In some embodiments, the opposite face of pawl 1056 is configured such that the pawl resists rotation of the thumb nut 1013 in the counter direction but can rise out of the groove 1058 if enough rotational force is applied to the thumb nut. In this way, the thumb nut can be counter rotated but the effort required to counter rotate the thumb nut is greater than the effort required to rotate the thumb nut in the dose-setting direction. In some embodiments, the opposite face of pawl 1056 is configured such that the pawl does not resist rotation of the thumb nut 1013 or, at most, resists counter rotation to the same degree as it resists rotation in the dose-setting direction. In this way, the ratchet provides aural and/or tactile feedback but does not generally favor rotation in one direction or the other.

Figure 20A:
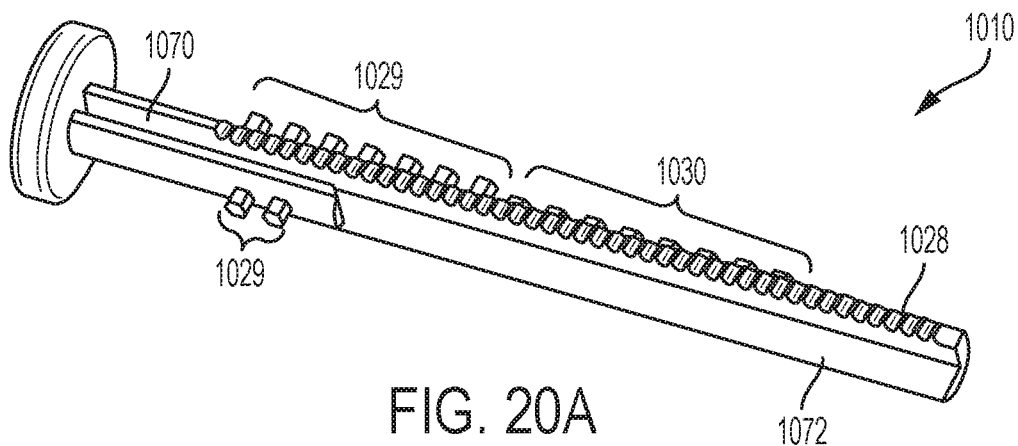
FIG. 20A illustrates a plunger rod, according to an embodiment.
Figure 20B:
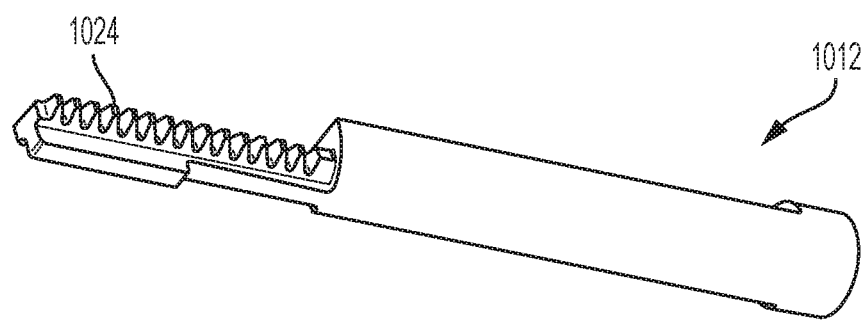
FIGS. 20B and 20C illustrate a drive rod, according to an embodiment.
Figure 20C:
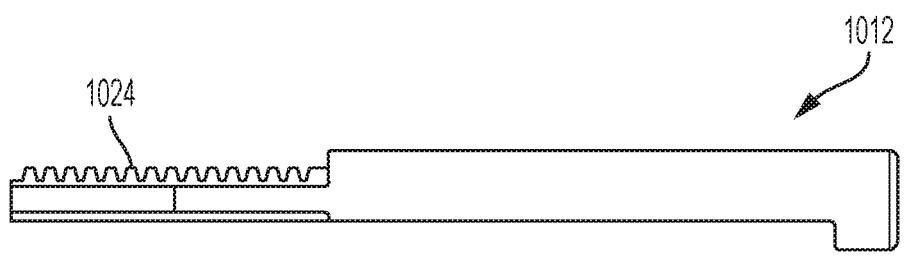

FIG. 20A is a perspective view of a plunger rod 1010, according to some embodiments. Plunger rod 1010 includes spacing pegs 1030 for maintaining the lateral position of plunger rod 1010 within syringe barrel 1009, as discussed above. Plunger rod 1010 includes a longitudinal groove 1070 along a portion of the shaft nearest the thumb rest 1038. Portions of the low and high force gears are located within this groove when the plunger rod subassembly is assembled. Plunger rod 1010 includes a cutout 1072 such that a cross section perpendicular to the longitudinal axis of plunger rod 1010 is semicircular. Cutout 1072 provides a bearing surface for a portion of drive rod 1012, which has a complimentary semicircular cross section, to slide along. Drive rod 1012, according to some embodiments, is shown in FIGS. 20B-C. Drive rod 1012 includes a set of linear gear teeth 1024, which engage the second set of teeth 1064B of higher force gear 1064. The cross-sectional profile of a portion of drive rod 1012 is configured to fit with and slide along the cutout 1072 of plunger rod 1010, providing a large bearing surface interface that can ensure smooth relative axial motion between the plunger rod and drive rod and reduced lateral play. Drive rod 1012 can include a cylindrical end portion to help concentrically locate drive rod 1012 in syringe barrel 1009.

Figure 21B:
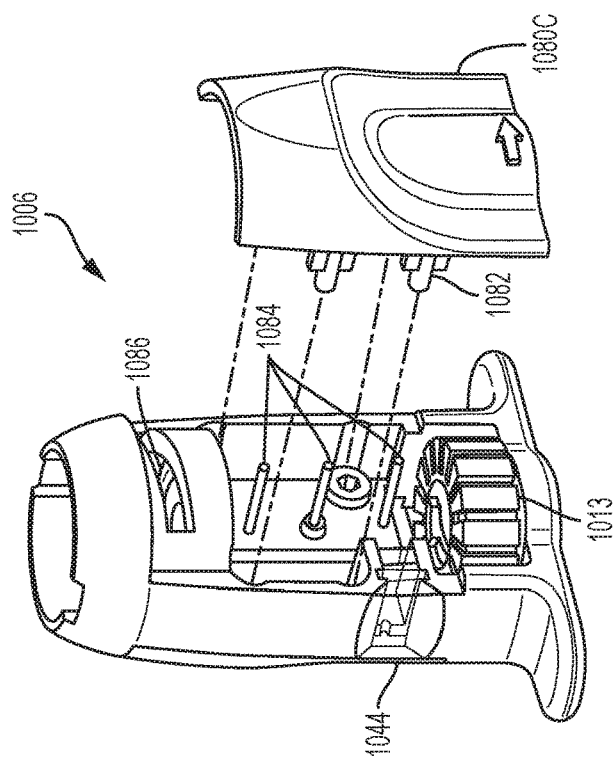
FIGS. 21A and 21B are exploded views illustrating aspects of an assembly process of a plunger rod subassembly, according to some embodiments.
Figure 21A:
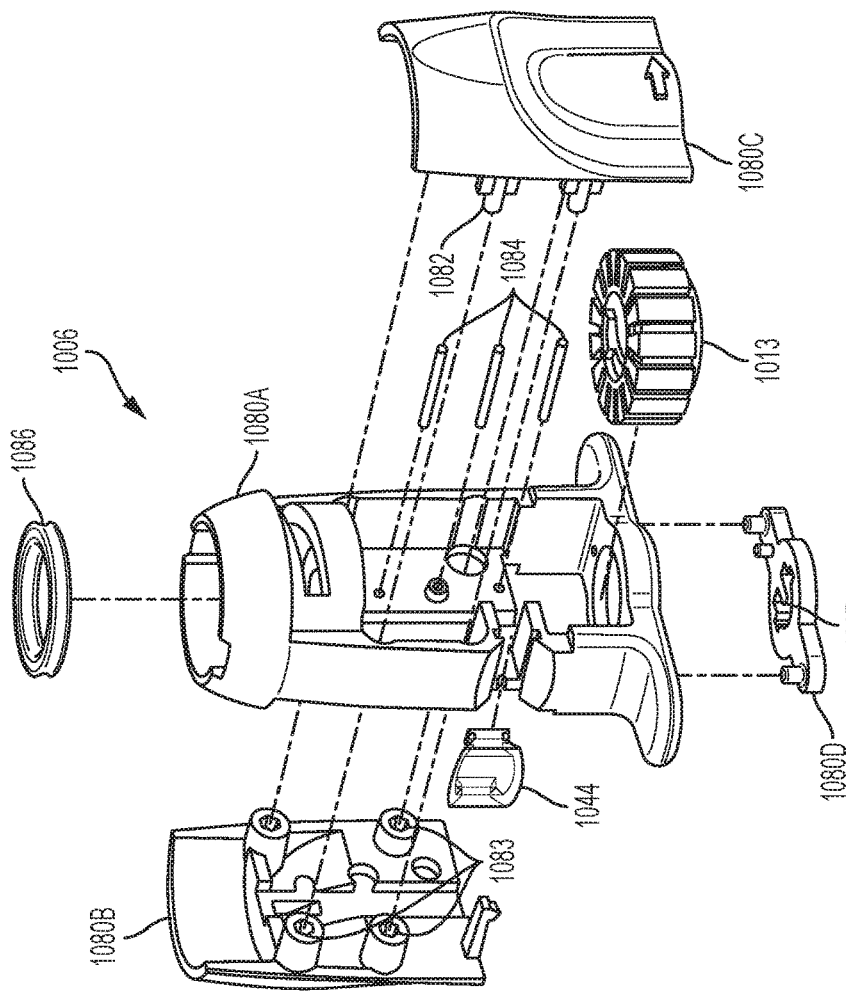

FIGS. 21A-B are exploded views illustrating aspects of the assembly process of plunger rod subassembly 1001, according to some embodiments. In the illustrated embodiment, housing 1006 includes four components—main body 1080A, back cover 1080B, front cover 1080C, and top cover 1080D. Pins 1082 in front cover 1080C fit into corresponding bores 1083 in back cover 1080B to assemble the front and back covers to the main body. Main body 1080A includes a plurality of holes into which gear pins 1084 are inserted. Gear pins 1084 provide shafts for the gears of the gear train 1011. Main body 1080A also includes grooves into which window 1044 slides. Top cover 1080D includes pins that fit into corresponding bores in the user end of main body 1080A. Top cover 1080D includes a cavity 1027 shaped to match the cross-sectional profile of plunger rod 1010, which can prevent rotation of plunger rod 1010, such that plunger rod 1010 can translate but not rotate. In some embodiments, a preloading ring 1086 may be provided to preload the engagement of plunger rod subassembly 1001 with the syringe barrel 1009. Preloading ring 1086 may be a coil spring, a wave spring, a ring of compliant material, such as plastic, foam, or rubber, or any other suitable component for preloading the engagement.

Following is a description of an assembly process for plunger rod subassembly 1001, according to some embodiments. The following process is intended to be exemplary only. Steps may be conducted in a different order, one or more of the steps may be omitted, and/or one or more additional steps may be included depending on the configuration of the various components of the particular embodiment. In a first step, top cover 1080D is seated and press-fit into main body 1080A, for example, using an arbor press. Next, the three gear pins 1084 are press-fit into the main body 1080A. Then, the thumb nut 1013 is inserted into the corresponding portion of main body 1080A, the back cover 1080B is seated onto the back side of the housing, and the preloading ring 1086 is inserted into the barrel opening of the housing. Next, the higher force gear 1064 is installed on the corresponding gear pin 1084—the gear pin farthest from the thumb nut 1013. The lower force gear 1062 is then installed onto the center gear pin 1084 and aligned such that its second set of gear teeth 1062B engage with the first set of gear teeth 1064A on higher force gear 1064. The drive rod 1012 is then inserted through the barrel opening in the housing 1006, aligned with alignment features of the housing, and pushed such that its teeth 1024 engage the second set of teeth 1064B on higher force gear 1064. The drive rod 1012 is inserted into the housing to a specified depth, which may depend on the particular application and which may be controlled using tooling.

In the next step, the plunger rod 1010 is inserted through the top cover 1080D and through the thumb nut 1013 until the lowest-most dosing lug 1029 prevents further insertion. The rotor gear 1060 is then installed onto the remaining gear pin 1084 and aligned for engagement with both the first set of teeth 1062A of the lower force gear 1062 and the teeth 1028 on plunger rod 1010. The thumb nut 1013 is rotated in the dose setting direction to engage the dosing lugs 1029 on plunger rod 1010 with the internal thread of thumb nut 1013. Plunger rod 1010 is translated further into the housing 1006 through continued rotation of thumb nut 1013 in the dose setting direction until plunger rod 1010 reaches a predetermined depth.

Next, window 1044 may be inserted into the corresponding groove in main body 1080A. The front cover 1080C is then aligned with features on the main body 1080A and/or features on back cover 1080B and press fit into place. This completes assembly of plunger rod subassembly 1001, according to some embodiments. The assembled plunger rod subassembly 1001 may then be assembled to a prefilled syringe or packaged, for example, for storage and/or shipment to the syringe filler for final assembly of a prefilled accurate and precise dosing syringe system.

Embodiments of the present invention may provide configurations which allow the use of standard, commercially-available components, thereby reducing overall manufacturing costs, streamlining assembly processes, and avoiding regulatory concerns often associated with non-standard materials and components. For example, syringe barrels may be made of plastic, glass, or any other material commonly used for medical grade products. One or more components may be made of any suitable plastic, such as polycarbonate (including those sold under the trade name "LEXAN" by SABIC Innovative Plastics of Pittsfield, Mass.) and the like. Any suitable elastomeric polymers or rubbers may be utilized (such as the rubber products sold under the trade name "HELVOET" by Datwyler Pharma Packaging USA Inc. of Pennsauken, N.J.) for components such as the plunger seal. Various medical grade metals, such as stainless steel, may be utilized for one or more components, such as the plunger rod, drive rod, gear pins, gears, thumb nut, etc., as will be appreciated by an ordinarily skilled artisan. Any of the components described herein may be shaped or sized in any configuration to meet desired parameters. Any of the components described herein may be formed as singular components or may comprise multiple sub-components. Components may be built and/or assembled by any suitable process, including using glues or welding methods such as ultrasonic welding.

A person of skill in the art will appreciate that dosing mechanisms, syringes, syringe systems, etc., according to the principles and features described herein, can generally be configured for any application including, injectable drug delivery into or onto the eye, intracellular delivery, delivery of radioactive agents, delivery of chemotherapy, etc.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A plunger rod assembly for a syringe comprising:
a first plunger rod component comprising a first linear gear and at least one protrusion;
a second plunger rod component comprising a second linear gear;
a first rotational gear that is translationally fixed and comprises a plurality of gear teeth for engaging the first linear gear;
a second rotational gear that is translationally fixed and comprises a second plurality of gear teeth for engaging the second linear gear, wherein the first rotational gear is coupled to the second rotational gear such that translation of the first plunger rod component causes translation of the second plunger rod component; and
a rotational component that engages the at least one protrusion of the first plunger rod component to translate the first plunger rod component to set the dose, wherein an axis of rotation of the rotational component extends in a direction of travel of the first plunger rod component.

2. The plunger rod assembly of claim 1, wherein translation of the first plunger rod component a first amount causes translation of the second plunger rod component a second amount that is less than the first amount.

3. The plunger rod assembly of claim 1, wherein the first rotational gear and the second rotational gear are portions of a compound gear.

4. The plunger rod assembly of claim 1, wherein the first rotational gear is spaced from the second rotational gear.

5. The plunger rod assembly of claim 4, wherein the first and second rotational gears are spaced by a third rotational gear.

6. The plunger rod assembly of claim 5, wherein the second and third rotational gears are compound gears.

7. The plunger rod assembly of claim 1, wherein the first set of gear teeth has a first pitch diameter and the second set of gear teeth has a second pitch diameter that is different from the first pitch diameter.

8. The plunger rod assembly of claim 1, wherein at least a portion of the first plunger rod component comprises a semicircular cross section and at least a portion of the second plunger rod component comprises a complimentary semicircular cross section.

9. The plunger rod assembly of claim 1, wherein the first plunger rod component is configured to axially translate in response to a force having an axial component applied directly to the first plunger rod component after the rotational component disengages from the at least one protrusion.

10. The plunger rod assembly of claim 1, wherein the rotational component comprises at least one stop that engages one of the at least one protrusion when the plunger rod component reaches an axial position relative to the rotational component.

11. The plunger rod assembly of claim 1, wherein the assembly comprises at least one ratchet component that is engaged with the rotational component such that the rotational component rotates more freely in a first direction than in a second direction.

12. The plunger rod assembly of claim 1, wherein the assembly comprises a housing for mounting on an end of a syringe barrel.

13. The plunger rod assembly of claim 12, wherein the assembly comprises a retainer for engaging with the housing and the end of the syringe barrel for affixing the plunger rod assembly to the end of the syringe barrel.

14. A syringe comprising:
a barrel;
a delivery conduit;
a plunger seal disposed within the barrel; and
a plunger rod assembly affixed to an end of the barrel, the plunger rod assembly comprising:
a first plunger rod component comprising a first linear gear and at least one protrusion;
a second plunger rod component disposed at least partially in the barrel and engaged with the plunger seal, wherein the second plunger rod component comprises a second linear gear;
a first rotational gear that is translationally fixed and comprises a plurality of gear teeth for engaging the first linear gear;
a second rotational gear that is translationally fixed and comprises a second plurality of gear teeth for engaging the second linear gear, wherein the first rotational gear is coupled to the second rotational gear such that translation of the first plunger rod component causes translation of the second plunger rod component; and
a rotational component that engages the at least one protrusion of the first plunger rod component to translate the first plunger rod component to set the dose, wherein an axis of rotation of the rotational component extends in a direction of travel of the first plunger rod component.

15. The syringe of claim 14, wherein the syringe is a prefilled syringe.

16. A blister pack comprising the pre-filled syringe of claim 15, wherein the syringe has been sterilized using EtO, H2O2, NO2 or Vaporized Peracetic Acid.

17. The blister pack of claim 16, wherein the outer surface of the syringe has at most 1 ppm EtO, H2O2, NO2 or Vaporized Peracetic Acid.

18. The blister pack of claim 16, wherein the total EtO, H2O2, NO2 or Vaporized Peracetic Acid residue on the outside of the syringe and inside of the blister pack is at most 0.1 mg.

19. The blister pack of claim 16, wherein the syringe has been sterilized with a Sterility Assurance Level of at least 10-6.

20. The syringe of claim 14, wherein the delivery conduit comprises an attached needle, an attachable needle, an IV connector, an attachable tubing connector, or an attachable microneedle array.

21. A method of delivering a dosage using a syringe that includes a barrel, a delivery conduit, a plunger seal disposed within the barrel, and a plunger rod assembly affixed to an end of the barrel, wherein the plunger rod assembly includes: a first plunger rod component comprising a first linear gear, a second plunger rod component disposed at least partially in the barrel and engaged with the plunger seal, wherein the second plunger rod component comprises a second linear gear, a first rotational gear that is translationally fixed and comprises a plurality of gear teeth for engaging the first linear gear, and a second rotational gear that is translationally fixed and comprises a second plurality of gear teeth for engaging the second linear gear, wherein the first rotational gear is coupled to the second rotational gear such that translation of the first plunger rod component causes translation of the second plunger rod component, wherein the first plunger rod component comprises at least one protrusion, and the assembly further comprises a rotational component for engaging the at least one protrusion to translate the first plunger rod component to set the dose, wherein an axis of rotation of the rotational component extends in a direction of travel of the first plunger rod component, the method comprising:

while pointing the delivery conduit of the syringe upwards with respect to the barrel, advancing the plunger seal within the barrel by rotating the rotational component;

setting a dosage by continuing to rotate the rotational component until the rotational component disengages from the first plunger rod component; and after the rotational component disengages from the first plunger rod component, delivering the dosage by applying a user force directly to an end of the first plunger rod component to advance the plunger seal.

22. The method of claim 21, comprising attaching a needle to the syringe prior to advancing the plunger seal within the barrel by rotating the second rotational component.

23. The method of claim 21, wherein the syringe is a prefilled syringe.

24. The method of claim 23, wherein the prefilled syringe is filled with a drug used for ophthalmic applications.

25. The method of claim 23, wherein the number of 10 micrometer or larger sized sub-visible particulates are less than 50 per milliliter of drug solution.

26. The method of claim 23, wherein the number of 25 micrometer or larger sized sub-visible particulates are less than 5 per milliliter of the drug solution.

27. The method of claim 23, wherein the number of 50 micrometer or larger sized sub-visible particulates are less than 2 per milliliter of the drug solution.

* * * * *